United States Patent [19]
Ito et al.

[11] Patent Number: 5,726,750
[45] Date of Patent: Mar. 10, 1998

[54] NON-DESTRUCTIVE TASTE CHARACTERISTICS MEASURING APPARATUS AND TRAY USED IN THE APPARATUS

[75] Inventors: Masahiro Ito; Junji Iida; Akira Terashima; Kazuo Maeda; Shuji Suzuki, all of Chiba; Takeo Ide; Toshiki Kishimoto, both of Tokyo, all of Japan

[73] Assignee: Sumitomo Metal Mining Co., Ltd., Tokyo, Japan

[21] Appl. No.: 668,337

[22] Filed: Jun. 25, 1996

[30] Foreign Application Priority Data

| Jun. 29, 1995 | [JP] | Japan | 7-188061 |
|---|---|---|---|
| Jul. 29, 1995 | [JP] | Japan | 7-212404 |
| Mar. 1, 1996 | [JP] | Japan | 8-044614 |
| Mar. 1, 1996 | [JP] | Japan | 8-071085 |
| Mar. 1, 1996 | [JP] | Japan | 8-071086 |
| May 24, 1996 | [JP] | Japan | 8-153345 |
| May 24, 1996 | [JP] | Japan | 8-153346 |

[51] Int. Cl.$^6$ .................................. G01N 21/01
[52] U.S. Cl. .................. 356/244; 356/446; 209/587
[58] Field of Search ................... 356/244, 446; 209/576, 577, 587, 588, 912, 938, 939

[56] References Cited

U.S. PATENT DOCUMENTS

| 4,279,346 | 7/1981 | McClure et al. | 209/588 |
|---|---|---|---|
| 4,830,503 | 5/1989 | Hoda et al. | 356/446 |
| 5,089,701 | 2/1992 | Dull et al. | 250/341 |
| 5,324,945 | 6/1994 | Iwamoto et al. | 250/910 |

FOREIGN PATENT DOCUMENTS

| 1-216265 | 8/1989 | Japan . |
|---|---|---|
| 1-235850 | 9/1989 | Japan . |
| 1-301147 | 12/1989 | Japan . |
| 2-147940 | 6/1990 | Japan . |
| 3-48138 | 3/1991 | Japan . |
| 3-176645 | 7/1991 | Japan . |
| 4-104041 | 4/1992 | Japan . |
| 4-208842 | 7/1992 | Japan . |
| 5-34281 | 2/1993 | Japan . |
| 5-34335 | 2/1993 | Japan . |
| 5-172549 | 7/1993 | Japan . |
| 5-288674 | 11/1993 | Japan . |
| 6-15236 | 1/1994 | Japan . |

OTHER PUBLICATIONS

Sumio Kawano et al., Journal of The Japanese Society For Horticultural Science, No. 2, vol. 62, pp. 465-470, 1993.

*Primary Examiner*—Frank G. Font
*Assistant Examiner*—Zandra V. Smith
*Attorney, Agent, or Firm*—Armstrong, Westerman, Hattori, McLeland & Naughton

[57] ABSTRACT

A non-destructive taste characteristics measuring apparatus comprising trays and a measuring section provided in the course of a transport path and at which light is made incident on a vegetable or fruit to measure its taste characteristics, wherein the trays are each provided with at least two tray-side light passages one opening ends of which are so made as to come in contact with the vegetable or fruit and the other ends of which stand open outward at the bottom of the tray, and the measuring section has at least two measurement-side light passages one opening ends of which are positionally adjustable to the opening ends of the tray-side light passages at its part facing the bottom of said tray, and is provided with i) a means for making light incident on the vegetable or fruit through one of the measurement-side light passages and one of the tray-side light passages and ii) a detector which the light emergent from the vegetable or fruit enters through the other tray-side light passage and the other measurement-side light passage. The apparatus enables continuous measurement of taste characteristics such as sugar content and ripeness of vegetables and fruits at a high speed and a high precision without complicating the structure.

19 Claims, 31 Drawing Sheets

NON-DESTRUCTIVE TASTE CHARACTERISTICS MEASURING APPARATUS AND TRAY USED IN THE APPARATUS

BACKGROUND OF THE INVENTION

1. Field of the Invention

This invention relates to an apparatus for the non-destructive measurement of taste characteristics that can non-destructively and continuously one by one measure the taste characteristics such as sugar content and ripeness of vegetables and fruits including muskmelons, watermelons and pumpkins. More particularly, it relates to a non-destructive taste characteristics measuring apparatus that can measure the taste characteristics of vegetables and fruits at a high speed and in a high precision without complicating the structure of the measuring apparatus.

2. Description of the Related Art

Since vegetables and fruits are natural products, they commonly have qualities that are non-uniform between individuals, and their market price rises and falls depending on the grade of qualities. Since also vegetables and fruits having bruises are commercially less valuable, it is preferable to non-destructively examine the quality of vegetables and fruits one by one.

The quality examination of vegetables and fruits has hitherto mostly relied on manual operation. In recent years, however, with a progress in sensor technique, distribution technique and computer technology, automatic examination apparatus have become available which are advantageous in view of accuracy and processing speed.

In such quality examination, the examination of sugar content of vegetables and fruits which involves subjective factors has been behind in its mechanization, but it has become possible to make non-destructive measurement of sugar content of vegetables and fruits by the use of laser beams, ultraviolet rays, infrared rays, electromagnetic waves or the like (see, for example, Japanese Patent Applications Laid-open No. 1-216265, No. 1-235850, No. 2-147940, No. 4-104041, No. 4-208842, No. 5-34281, No. 5-172549 and No. 6-152836).

In such non-destructive measurement of sugar content of vegetables and fruits by means of automatic examination apparatus, a plurality of vegetables and fruits are successively transported at appropriate intervals, during which light rays such as laser beams, ultraviolet rays, infrared rays, electromagnetic waves or the like are made incident on the respective vegetables and fruits to pass the light from their outsides to insides at a measuring position provided in the course of transport, and the absorption of light in sugar is measured when the light is emergent from vegetables and fruits, to obtain data, on the basis of which the sugar content is converted into numerical values or indicated in ranks.

The vegetables and fruits such as muskmelons, watermelons and pumpkins have thick exocarps and have a larger size than grapes, oranges or the like. Hence, it is difficult to cause the incident light to deeply pass into such vegetables and fruits to obtain detection light (i.e., the light emergent from vegetables and fruits) with a sufficient intensity. If the light does not deeply pass into vegetables and fruits when made incident, the information obtained is only concerned with that of exocarps and the information of the insides of vegetables and fruits is relatively insufficient, so that no accurate sugar content can be detected. Accordingly, in order to accurately reflect the sugar content of the insides of vegetables and fruits upon the results of measurement, it is necessary to cause the light to deeply pass into the vegetables and fruits and also to use, when detected by a detector, the light emergent from their insides (i.e., detection light). In such a case, the light tends to attenuate inside the vegetables and fruits because of, e.g., absorption of light, so that the amount of detection light is necessarily small.

The fact that the amount of detection light is small means that the SN ratio tends to become poor when the background light such as sunlight and the light emitted from a light source and not transmitted through the insides of vegetables and fruits enter the detector, resulting in an increase in errors of the sugar content to be measured.

In order to increase the amount of detection light, one may contemplate increasing the power of the light to be made incident on the vegetables and fruits. Such an increase in power, however, may cause a burn of the surfaces of vegetables and fruits to make it difficult to carry out the non-destructive measurement.

Accordingly, a method has been conventionally studied in which as shown in FIG. 34 a pair of tubular members a and b at least are brought into pressure contact with the periphery of a fruit M (a muskmelon), and light is made incident on the fruit M through the tubular member a so that the light is made incident on the fruit M without leakage and only the light emergent from the fruit M enters a detector (not shown) through the tubular member b.

When the sugar content of vegetables and fruits is actually measured using the above tubular members a and b, these tubular members a and b must be moved in synchronization with the transport of the fruit M in order for the tubular members a and b to be provided in pressure contact with the fruit M that is being transported. Accordingly, it becomes necessary to incorporate the non-destructive sugar content measuring apparatus with a mechanism for moving these tubular members a and b. This has caused the problem that the measuring apparatus must be complicated in structure.

It is possible to omit the mechanism for moving these tubular members a and b, if the apparatus is incorporated with a mechanism for temporarily stopping the transport of vegetables and fruits when the sugar content of the vegetables and fruits is measured.

However, if the apparatus is set up with such constitution, it is impossible from a structural viewpoint to continuously measure the sugar content of vegetables and fruits, bringing about the problem of causing a decrease in measuring speed.

SUMMARY OF THE INVENTION

The present invention was made taking note of such problems. Accordingly, an object of the present invention is to provide a non-destructive taste characteristics measuring apparatus that can continuously measure the taste characteristics such as sugar content and ripeness of vegetables and fruits at a high speed and in a high precision without complicating the structure of the measuring apparatus.

Another object of the present invention is to provide a non-destructive taste characteristics measuring apparatus that can stably transport the measurement objects vegetables and fruits and also can individually measure light rays transmitted through different portions of the insides of vegetables and fruits.

Still another object of the present invention is to provide a non-destructive taste characteristics measuring apparatus that can prevent measurement errors from being caused by foreign matter that may adhere to the measurement objects vegetables and fruits.

A further object of the present invention is to provide a non-destructive taste characteristics measuring apparatus that can prevent measurement errors from being caused by leakage light when light is made incident on vegetables and fruits to measure their taste characteristics.

A still further object of the present invention is to provide a non-destructive taste characteristics measuring apparatus that has trays on which the measurement objects vegetables and fruits are placed, and can arrange the trays in a proper delivery direction at their measuring section when the trays are delivered to the transport path of the non-destructive taste characteristics measuring apparatus.

A still further object of the present invention is to provide a non-destructive taste characteristics measuring apparatus that has a plurality of measuring sections and can prevent any different measuring conditions at the respective measuring sections.

A still further object of the present invention is to provide a tray used for the measurement of taste characteristics, that can be delivered to the transport path of the non-destructive taste characteristics measuring apparatus without taking account of the direction of the tray with respect to the direction in which vegetables and fruits are transported, and also that can well transport vegetables and fruits and enables accurate positional control at the measuring section.

A still further object of the present invention is to provide a tray used for the measurement of taste characteristics, that has the above characteristic features and also has a structure that may hardly cause measurement errors.

To achieve the foregoing objects, the present invention provides a non-destructive taste characteristics measuring apparatus comprising a plurality of trays on which measurement objects vegetables and fruits are to be placed, a transport means for successively delivering the trays at appropriate intervals, and a measuring section provided in the course of a transport path and at which light is made incident on each vegetable or fruit so as to pass from the outside to the inside thereof and the intensity of light emergent from the vegetable or fruit is measured to determine the taste characteristics of the vegetables and fruits, wherein;

the trays are each provided in a vegetable or fruit holding part of the tray, with at least two tray-side light passages one opening ends of which are so made as to come in contact with the lower periphery of the vegetable or fruit and the other opening ends of which stand open outward at the bottom of the tray; the passages extending in the thickness direction of the tray at its part where the vegetable or fruit is held; and the measuring section has at least two measurement-side light passages one opening ends of which are positionally adjustable to the opening ends of the tray-side light passages within the transport path at its part facing the bottom of the tray, and is provided with i) a means for making light incident on the vegetable or fruit through one of the measurement-side light passages and one of the tray-side light passages which is positionally adjusted thereto and ii) a detector which the light emergent from the vegetable or fruit enters through the other tray-side light passage and the other measurement-side light passage positionally adjusted thereto, to measure the taste characteristics of the vegetable or fruit.

The tray of the present invention, used in the above non-destructive taste characteristics measuring apparatus, is a tray for a non-destructive taste characteristics measuring apparatus on which tray a vegetable or fruit is placed and which is delivered along a transport path of the non-destructive taste characteristics measuring apparatus so that the taste characteristics of the vegetable or fruit are measured by making light incident on the vegetable or fruit and measuring light emergent from the vegetable or fruit in a measuring section provided in the course of the transport path, and is not fixed to a transport means;

the tray comprising a cylindrical tray lower portion and a square column-like tray upper portion projecting upward from the cylindrical tray lower portion and not protruding outward from the circumferential edge of the cylindrical tray lower portion; the square column-like tray upper portion being provided at the top thereof with a holding part in a concave shape, and being provided in the holding part with two tray-side light passages; and the tray having a two-directional symmetry.

According to another embodiment, the tray according to the present invention comprises a cylindrical tray main body and a pair of planar portions formed by cutting two upper portions of the periphery of the tray main body in parallel to each other; the tray main body being provided at the top thereof with a holding part in a concave shape, and being provided in the holding part with two tray-side light passages; and the tray having a two-directional symmetry.

According to still another embodiment, the tray according to the present invention comprises a cylindrical tray lower portion and a square column-like tray upper portion projecting upward from the cylindrical tray lower portion and not protruding outward from the circumferential edge of the cylindrical tray lower portion; the square column-like tray upper portion being provided at the top thereof with a holding part in a concave shape, and being provided in the holding part with four tray-side light passages; and the tray having a four-directional symmetry.

These and other features and advantages of the present invention are described in or will become apparent from the following detailed description of the preferred embodiments.

DESCRIPTION OF THE PREFERRED EMBODIMENTS

Figure 1:
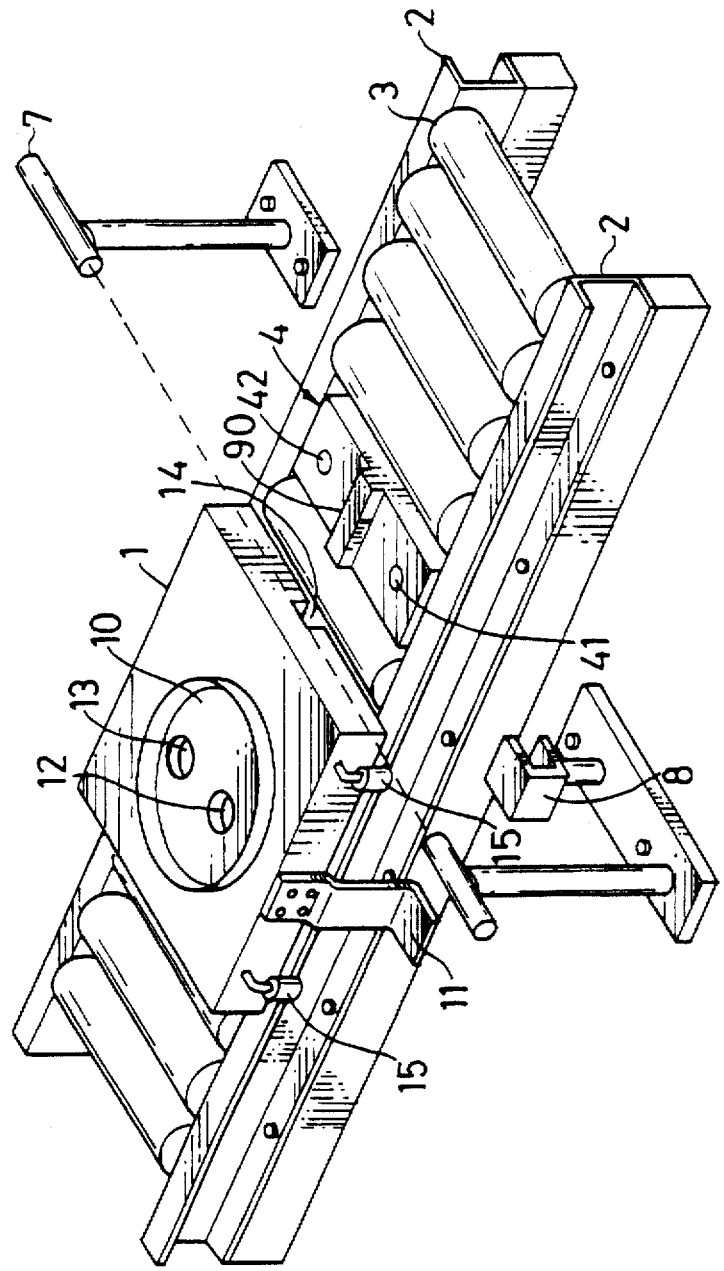
FIG. 1 is a perspective illustration of the main part of a non-destructive taste characteristics measuring apparatus according to Example 1.

The present invention will be described below in greater detail.

The non-destructive taste characteristics measuring apparatus of the present invention basically has a plurality of trays on which measurement objects vegetables and fruits are to be placed, a transport means for successively delivering the trays at appropriate intervals, and a measuring section provided in the course of a transport path and at which light is made incident on each vegetable or fruit so as to pass from the outside to the inside thereof and light emergent from the vegetable or fruit is detected to continuously measure the taste characteristics of the vegetables and fruits, and is basically characterized by the following:

The trays are each provided in a vegetable or fruit holding part of the tray, with at least two tray-side light passages one opening ends of which are so made as to come in contact with the lower periphery of the vegetable or fruit and the other opening ends of which stand open outward at the bottom of the tray. These passages extend in the thickness direction of the tray at its part where the vegetable or fruit is held.

The measuring section has at least two measurement-side light passages one opening ends of which are positionally adjustable to the opening ends of the tray-side light passages within the transport path at its part facing the bottom of the tray.

The measuring section is also provided with i) a means for making light incident on the vegetable or fruit through one of the measurement-side light passages and one of the tray-side light passages which is positionally adjusted thereto and ii) a detector which the light emergent from the vegetable or fruit enters through the other tray-side light passage and the other measurement-side light passage positionally adjusted thereto, to measure the taste characteristics of the vegetable or fruit.

According to the present non-destructive taste characteristics measuring apparatus, the light is incident on the vegetable or fruit through one measurement-side light passage of the measuring section and through one tray-side light passage provided in the holding part of each tray and the light emergent from the vegetable or fruit enters the detector through the other tray-side light passage also provided in the holding part of the tray and through the other measurement-side light passage of the measuring section. Hence, the light can be prevented from leaking when the light is incident on the vegetable or fruit and enters the detector. Thus, the light can be passed into the vegetable or fruit in a good efficiency and also the light emergent from the vegetable or fruit can enter the detector in a good efficiency. This makes it possible to properly and highly precisely measure the sugar content and so forth of vegetables and fruits without increasing the power of the light made incident on the vegetables and fruits.

The tray-side light passages, which correspond to the conventional tubular members, are provided in the holding part of the tray. Hence, it is unnecessary to provide any moving mechanism for the tubular members which otherwise must be moved in synchronization with the transport of vegetables and fruits, so that the sugar content and so forth can be measured at a high speed and a high precision without complicating the structure of the measuring apparatus.

In the non-destructive taste characteristics measuring apparatus of the present invention, a light incidence timing control means is necessary which makes the light incident on the vegetable or fruit at the time of point where the opening ends on the measuring section side, of the tray-side light passages provided in the holding part of the tray come into positional agreement with the opening ends on the tray side, of the measurement-side light passages provided in the measuring section. Such a light incidence timing control means may be constituted of, for example, a detectee member provided at any common position of the tray, a sensor that is provided in the vicinity of the measuring section and detects the presence of the detectee member of the tray when the opening ends of the tray-side light passages come into positional agreement with the opening ends of the measurement-side light passages, and a power source switching means that on-off operates a light source serving as the light incidence means, in accordance with detection signals from the sensor.

With regard to the number of the tray-side light passages and measurement-side light passages respectively provided in the holding part of the tray and the measuring section, they must be at least two passages, one of which is a passage for the light incident on the vegetable or fruit and the other of which is a passage for the light emergent from the vegetable or fruit. Three tray-side light passages and three measurement-side light passages may also be provided. In such an embodiment, the vegetable or fruit can be three-point supported by the aid of the three opening ends of the tray-side light passages, so that the vegetable or fruit can be stably transported, and also one passage can be used for the light incident on the vegetable or fruit and the remaining two passages for the light emergent from the vegetable or fruit, so that the sugar content and so forth can be measured in an improved precision. More specifically, since the sugar content and so forth may be in non-uniform distribution inside the natural products vegetables and fruits, more accurate measurement can be made when light rays having passed through different portions in the interior of a vegetable or fruit are individually measured to determine an average value of the taste characteristics such as sugar content and ripeness.

For the same purpose, the measuring apparatus of the present invention may be constituted of four tray-side light passages and four measurement-side light passages, where light rays having the same wavelengths are made incident on the vegetable or fruit through two measurement-side light passages and the two tray-side light passages positionally adjusted thereto and also light rays emergent from the vegetable or fruit enter two detectors through the remaining two tray-side light passages and two measurement-side light passages positionally adjusted thereto.

In such an embodiment, the measuring apparatus may also be constituted of four tray-side light passages provided in the tray, and the measuring section has two measurement-side light passages opening ends of which are positionally adjustable to each two sets of the opening ends of the respective tray-side light passages, where the measuring section is provided with i) a means for successively making light rays incident on the vegetable or fruit through one measurement-side light passage and two tray-side light passages successively positionally adjusted thereto and ii) a detector which the light emergent from the vegetable or fruit successively enters through the remaining two tray-side light passages and the other measurement-side light passage successively positionally adjusted thereto.

The non-destructive taste characteristics measuring apparatus of the present invention has the structure wherein the light is made incident on the vegetable or fruit placed on the holding part of the tray, through one of the measurement-side light passages provided beneath the tray and through one of the tray-side light passages and the light emergent from the vegetable or fruit enters the detector provided beneath the tray, through the other tray-side light passage and measurement-side light passage to measure the taste characteristics such as sugar content. Hence, there is a possibility that any dust or dirt having adhered to vegetables and fruits comes off during the measurement to clog the measurement-side light passages of the measuring section, causing measurement errors. For this reason, a light-transmissive cover member that covers the respective tray-side opening ends of the measurement-side light passages may preferably be provided on the measuring section over its surface facing the tray. This light-transmissive cover member may also preferably be provided with a cleaning means for removing the foreign matter having adhered to this member. Such a light-transmissive cover member may be made of a material as exemplified by glass and plastic. The cleaning means may include a cleaning brush, where, for example, the light-transmissive cover member may be formed of a rotatable disc-like plate and may be provided in the manner that its rotational center is set aside in the vicinity of the tray-side opening ends of the measurement-side light passages, and the cleaning brush may be provided in the manner that its upper and lower brush tips come in touch with the top and bottom surfaces of the light-transmissive cover member on its side that is opposite to one opening end of the measurement-side light passages around the rotational center. Alternatively, the cleaning means may be constituted of an air blow means that blows air against the top and bottom surfaces of the light-transmissive cover member to remove the foreign matter.

Incidentally, in the present non-destructive taste characteristics measuring apparatus, there is a possibility that light leaks from gaps formed between the opening ends of the tray-side light passages and the periphery of a vegetable or fruit when the measurement objects vegetables and fruits such as muskmelons have too small external size or the nets present on the surface of such a vegetable or fruit form too large hills and valleys. Such leakage light may cause a little lowering of the measurement precision.

Accordingly, in order to prevent such leakage light, a pad member may be provided at each opening end of the tray-side light passages on its side where the vegetable or fruit is placed. The pad member may be formed of a porous material, and be capable of being deformed by the weight of the vegetable or fruit when it is placed on the tray, to close the gaps between the periphery of the vegetable or fruit and the opening ends of the tray-side light passages. As the material that makes up this pad member, any porous materials may be used so long as they have the action of being deformed by the weight of the vegetable or fruit when it is placed on the tray, to close the gaps between the periphery of the vegetable or fruit and the opening ends of the tray-side light passages. Such materials may include, for example, urethane rubber (trade name: SORBOTHANE; available from Sanshin Kosan K.K.). A porous material specified by a trade name "α-GEL" (available from Sigel Co.) may also be used. This pad member is formed substantially in a ring so that no difficulty may arise when the light passes through the interior of the tray-side light passages, and is also provided via an appropriate adhesive at the opening ends of the tray-side light passages on their side where the vegetable or fruit is placed.

Figure 35:
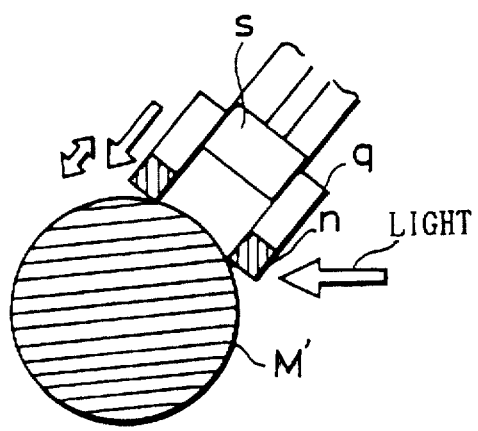
FIG. 35 illustrates a test method used to determine how the amount of light leaking from the gap between a vegetable or fruit and a pad member varies depending on the magnitude of the weight applied to the pad member.
Figure 36:
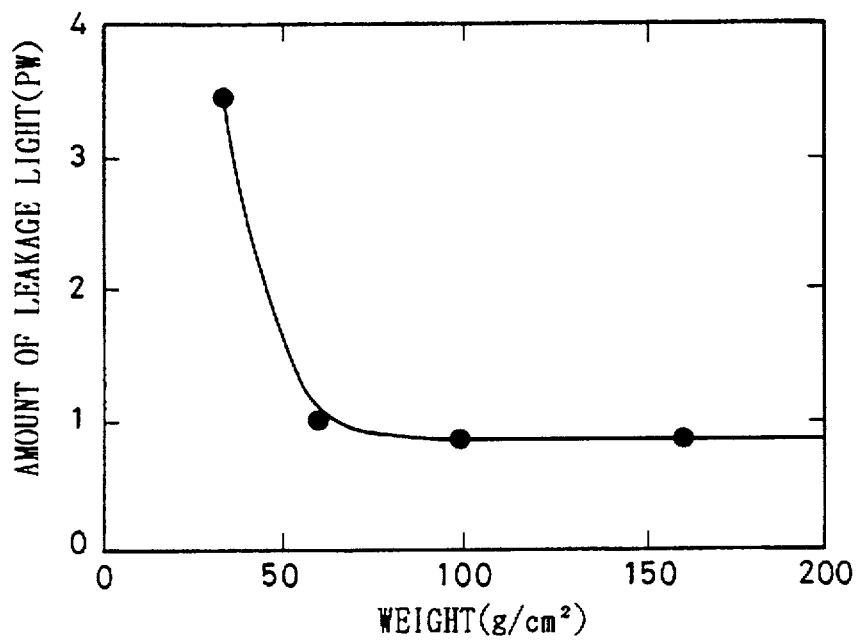
FIG. 36 is a graph showing the relationship between the weight and the amount of leakage light, determined by the test method shown in FIG. 35.

FIG. 35 diagrammatically illustrates a test method used to determine how the amount of light leaking from the gaps between the vegetable or fruit and the pad member varies depending on the magnitude of the weight applied to act on the pad member. More specifically, a cylinder q fitted with a ring-like pad member n made of urethane rubber is provided in pressure contact with a muskmelon model M' made up using a light-non-transmissive material, and light is made to enter through a gap between the muskmelon model M' and the pad member n. The amount of light leaking from this gap into the cylinder q is measured using a sensor s to determine the relationship between the magnitude of the weight applied to act on the pad member n and the amount of leakage light (pW). FIG. 36 is a graph showing the results thus obtained. It has been confirmed from this graph that a force of about 60 g/cm² or above may be acted on the pad member in order to prevent the leakage light. Here, muskmelons are usually about 1 kg to about 2.5 kg in weight. In the case of watermelons, some large ones are about 10 kg in weight. The total area in which the pad member comes in contact with the vegetable or fruit such as a muskmelon depends on the opening areas of the tray-side light passages, and usually it is about 15 cm² at largest. Hence, even in the case when the lightest muskmelon is placed on the holding part of the measuring apparatus, it follows that 1,000 g/15 cm²=67 g/cm². Thus, it is confirmed that the leakage light can be well prevented by the action of the pad member provided at the opening ends of the tray-side light passages.

Figure 37:
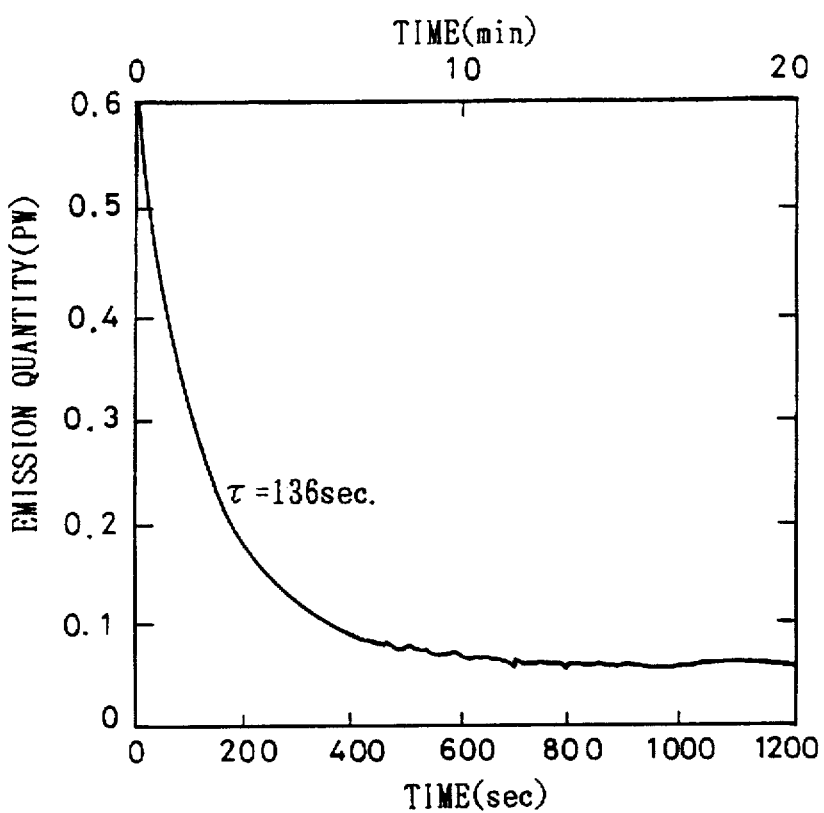
FIG. 37 is a graph showing the relationship between time and emission quantity, of fluorescence emitted from vegetables and fruits on which visible light has been made incident.

Vegetables and fruits having green rinds as exemplified by muskmelons, watermelons and pumpkins have the features that they absorb light of 700 nm or below on their surfaces and exhibit fluorescence with a long lifetime. FIG. 37 is a graph showing the relationship between the amount of fluorescent emission and the time, the former being detected when visible light is made incident on muskmelons and, after the visible light has been put off, the fluorescence emitted from muskmelons is detected using a sensor. It is confirmed from this graph that the time τ by which the fluorescence attenuates to 1/e is 136 seconds and the time by which it is no longer seen is about 5 minutes to about 10 minutes. Hence, there is a possibility that measurement errors caused by this fluorescence occur when the taste characteristics such as sugar content and ripeness on vegetables and fruits exposed to fluorescent lamps, sunlight or the like for a long time are measured as they are, by the non-destructive taste characteristics measuring apparatus of the present invention. Accordingly, with regard to the vegetables and fruits that exhibit fluorescence, the measurement may preferably be made after they have been stored for 5 to 10 minutes in a dark room, or in such a state that filters for cutting short wavelength visible light (700 nm or below) are put to fluorescent lamps or electric lamps, as well as windows and so forth in the room where the measuring apparatus is installed, so as for the vegetables and fruits not to be exposed to light of 700 nm or below.

The light leaking from the tray-side light passages can be very well prevented by the action of the pad member described above. There, however, is a possibility that, even though such a pad member is provided, it can not well function and the light may leak from the opening ends of the tray-side light passages when the measurement objects vegetables and fruits have extremely large size or small size.

For example, with regard to the structure of the holding part of the tray, gaps tend to be formed between the periphery of a vegetable or fruit and the pad member when the holding part has such a structure that the periphery of the vegetable or fruit is brought into contact with the inner side where the opening ends at the respective tray-side light passages are adjacent to each other (i.e., the inside area of the opening ends at the respective tray-side light passages) to support the vegetable or fruit. Although there is no problem in the region where the opening ends at the tray-side light passages come in contact with the inward periphery of the vegetable or fruit (i.e., the region corresponding to the side where the respective opening ends at the tray-side light passages are adjacent to each other), the gaps more tend to be produced with a decrease in external size of vegetables and fruits, in the region where the respective opening ends do not come in contact with the outward periphery of the vegetable or fruit (i.e., the region corresponding to the side opposite to the side where the respective opening ends at the tray-side light passages are adjacent to each other). When the gaps are formed at such portions, part of the light incident on the vegetable or fruit leaks from the gaps, and the leakage light passes along the periphery of the vegetable or fruit to unwantedly enter the vegetable or fruit from the opposite-side opening ends of the tray-side light passages, to cause measurement errors.

Now, in order to more safely prevent such leakage light, the pad member may be provided on the side of each opening end of the tray-side light passages via a contractible tubular member communicating with each tray-side light passage.

More specifically, this contractible tubular member flexibly acts in accordance with the differences in size of the measurement objects vegetables and fruits. For example, in the case when the holding part of the tray has the above structure that the periphery of the vegetable or fruit is brought into contact with the inside area of the opening ends at the respective tray-side light passages, the contractible tubular member is pressed against a large-size vegetable or fruit by the weight and contracts on its side coming in touch with the outer surface of the vegetable or fruit. On the other hand, against a small-size vegetable or fruits, it expands upward on its outer side because the pressure is weak, and push up the pad member on the side coming in touch with the outer surface of the vegetable or fruit. Hence, without regard to the differences in size of vegetables and fruits, it becomes possible to surely close the gaps between the periphery of the vegetable or fruit and the opening ends of the tray-side light passages by the action of contraction and expansion of the contractible tubular member. Such a contractible tubular member can be exemplified by a tubular member comprised of a linear material folded into a spiral and a tubular material that covers the outer surface of the spiral.

The measurement errors caused by the leakage light may occur also when part of the light emitted toward the vegetable or fruit through one measurement-side light passages enters the other measurement-side light passage via the gap between the tray and the measuring section. In order to prevent such leakage light, a leakage light preventing means may be provided on the surfaces facing each other between the tray and the measuring section, which is a means by which the light incident on the vegetable or fruit through the tray-side light passage and the measurement-side light passage positionally adjusted thereto is prevented from leaking into other measurement-side light passage.

Figure 2:
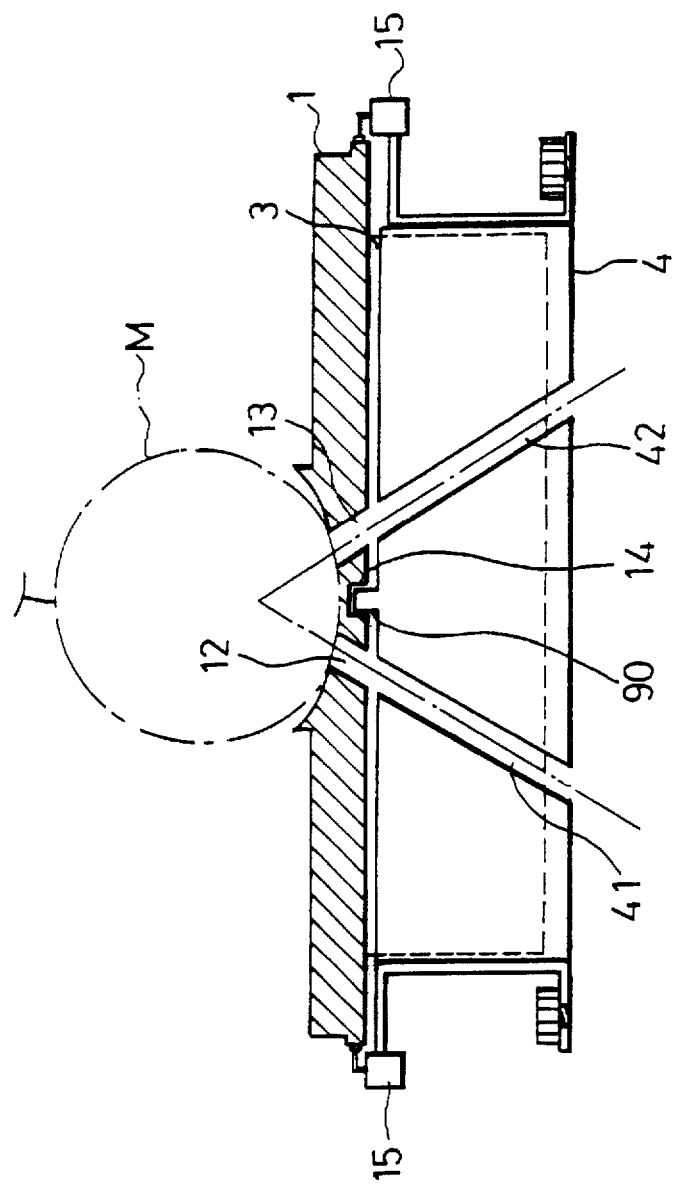
FIG. 2 is a cross-sectional illustration of the tray and measuring section shown in FIG. 1.

Such a leakage light preventing means may be constituted of, as shown in FIG. 1 or 2, a linear projection 90 provided on the top of the measuring section along its tray delivery direction and a linear recession 14 provided in the bottom of the tray on the side of the measuring section and slidably loosely fitted to the linear projection.

In the embodiment where this leakage light preventing means is incorporated in the apparatus, the linear projection provided on the top of the measuring section and the linear recession provided in the bottom of the tray may also be utilized to constitute a tray direction control means. More specifically, since in the present apparatus the trays on which vegetables and fruits are placed are delivered to the inside of the transport path along which the measuring section is provided, the trays must be delivered to the measuring section in the direction put in proper order. This is because the opening ends of the tray-side light passages in the tray must be positionally adjusted to the opening ends of the measurement-side light passages in the measuring section. Accordingly, the above linear projection and linear recession may be utilized to constitute the tray direction control means as described below.

Figure 30:
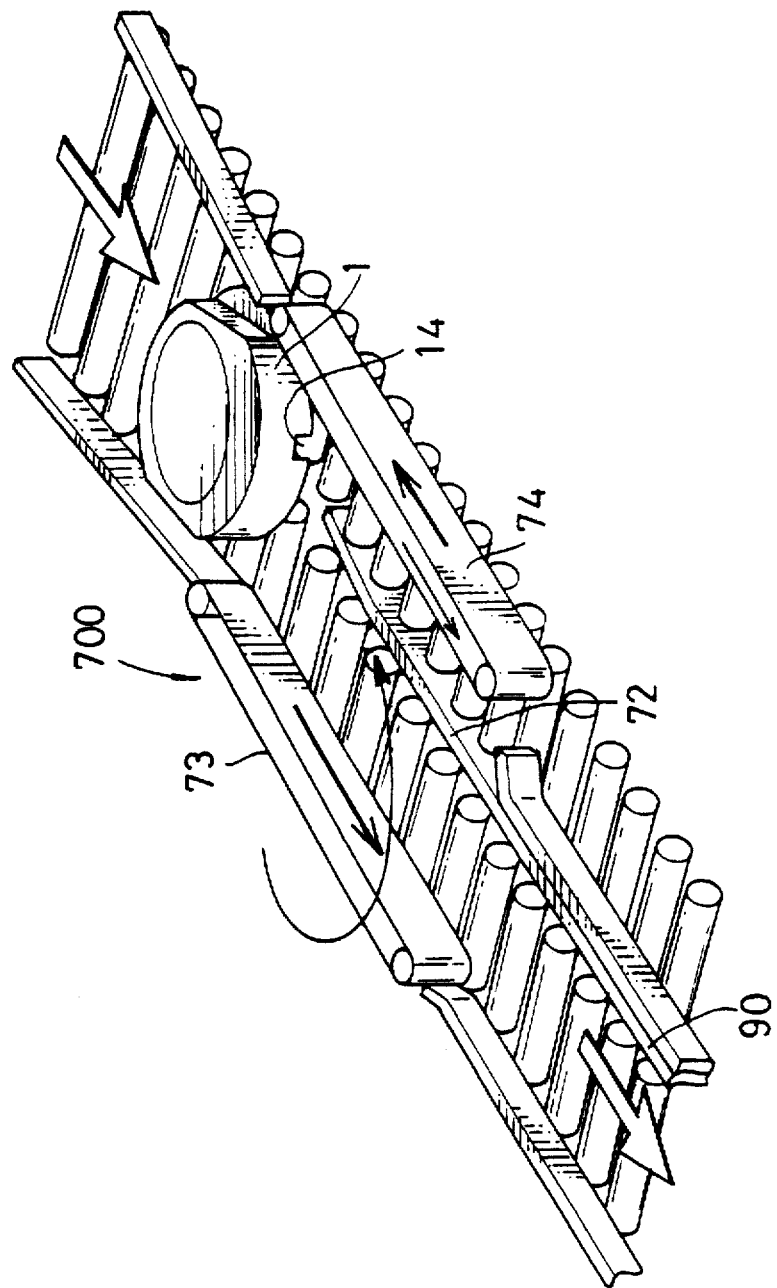
FIG. 30 is a perspective illustration of a tray direction control means incorporated in the non-destructive taste characteristics measuring apparatus according to Example 12.

This tray direction control means may be constituted of, as shown in FIG. 30, a projected guide provided at the middle of the width direction of the transport path in its tray delivery direction and so provided as to be loosely fitted to the linear recession positionally adjustable to the linear projection and formed in the bottom of the tray, and at least a pair of delivery means (e.g., belt means) provided on both side edges of the transport path where the projected guide is provided and capable of coming in contact with the side walls of the tray and being driven at different delivery speeds. In the embodiment where this tray direction control means is provided at the lead-in portion of the transport path where the measuring section is provided, the tray runs up on the projected guide and is sent forward while being turned by the action of the delivery means. Then, at the time when the projected guide comes into agreement with the linear recession of the tray, the linear recession is loosely fitted to the the projected guide. After the former has been loosely fitted to the latter, the tray is further sent forward in the state where the projected guide has been loosely fitted to the linear recession, so that at the measuring section the tray delivery direction can be put in proper order. The pair of delivery means may preferably be driven at such speeds that establish the relationship of (V1+V2)/2=V0 wherein V1 represents a delivery speed of one of them, V2 represents a delivery speed of the other and V0 represents a delivery speed at the transport path at its part other than the tray direction control means.

In the present non-destructive taste characteristics measuring apparatus, the detector that detects the light emergent from the vegetables and fruits is provided usually in the manner it is fixed to the inside of a measurement-side light passage or the opening end of the measurement-side light passage. Hence, the distance between the surface of the measurement object vegetable or fruit and the detector delicately varies depending on the size of the vegetable or fruit placed on the holding part of the tray (i.e., when the vegetable or fruit has a smaller external size, the distance from the detector is larger than the case when it has a large external size). Hence, even when the pad member and leakage light preventing means described above are provided to prevent the light from leaking from the opening ends of the tray-side light passages or prevent part of the incident light from leaking into other measurement-side light passage, there is a possibility that measurement precision may become non-uniform depending on the differences in size of the vegetables and fruits because the amount of light entering the detector may vary because of, e.g., the absorption of light in the inner peripheral walls of the tray-side light passage and measurement-side light passage as the distance between the vegetable or fruit and the detector varies.

To cope with this matter, the inner peripheral walls of the tray-side light passage and measurement-side light passage may be endowed with a high light-reflectivity. More specifically, when the inner peripheral walls are endowed with a high light-reflectivity, the absorption of light in the inner peripheral walls of the tray-side light passage and measurement-side light passage less occurs even when the distance between the vegetable or fruit and the detector varies depending on the differences in size of the measurement objects vegetables and fruits, and the amount of light entering the detector may vary with difficulty, so that it becomes possible to prevent non-uniform measurement precision. As methods by which the inner peripheral walls of the tray-side light passage and measurement-side light passage is endowed with a high light-reflectivity, for example, the inner peripheral walls may be plated with a metal such as gold, or the tray-side light passage and measurement-side light passage themselves are formed of a metallic material having a high light-reflectivity.

The tray of the present invention, used in the non-destructive taste characteristics measuring apparatus described above has two-directional symmetry or four-directional symmetry, has a good delivery performance when delivered in the transport path at its part other than the measuring section, and also has the performance to enable accurate positional control of trays in the transport path.

More specifically, the tray of the present invention, used in the non-destructive taste characteristics measuring apparatus described above is a tray for a non-destructive taste characteristics measuring apparatus on which tray a vegetable or fruit is placed and which is delivered along a transport path of the non-destructive taste characteristics measuring apparatus so that the taste characteristics of the vegetable or fruit are measured by making light incident on the vegetable or fruit and measuring light emergent from the vegetable or fruit in a measuring section provided in the course of the transport path, and is not fixed to a transport means, which tray is characterized by the following.

That is, the tray comprises a cylindrical tray lower portion and a square column-like tray upper portion projecting upward from the cylindrical tray lower portion and not protruding outward from the circumferential edge of the cylindrical tray lower portion; the square column-like tray upper portion being provided at the top thereof with a holding part in a concave shape, and being provided in the holding part with two tray-side light passages; and the tray has a two-directional symmetry.

According to this tray, the tray has a two-directional symmetry on the whole. Hence, when trays on which vegetables and fruits are placed are delivered into the transport path manually or mechanically, they can be delivered without so much taking care of the directions of trays with respect to their delivery direction. Also, the tray has a structure wherein the square column-like tray upper portion does not protrude outward from the circumferential edge of the cylindrical tray lower portion, and hence, when delivered in the transport path at its part other than the measuring section, the portions at which the respective trays for the measurement of taste characteristics come in contact with one another or come in contact with the wall surfaces of the transport path are the peripheries of their cylindrical tray lower portions, and their contact area can be minimized, so that they can be delivered in a good performance. In addition, the square column-like tray upper portion has four flat surfaces serving as reference surfaces, and hence, when delivered through the measuring section provided in the course of the transport path, any of the four flat surfaces of the tray upper portion may be allowed to engage with a guide provided at the measuring section, so that it becomes possible to make accurate positional control at the measuring section.

The tray may alternatively have a structure wherein the cylindrical tray lower portion and the square column-like tray upper portion are inversed, or a structure wherein a square column-like tray middle portion is provided between cylindrical tray lower and upper portions.

More specifically, the tray may comprise a cylindrical tray upper portion and a square column-like tray lower portion projecting downward from the cylindrical tray upper portion and not protruding outward from the circumferential edge of the cylindrical tray upper portion; the cylindrical tray upper portion being provided at the top thereof with a holding part in a concave shape, and being provided in the holding part with two tray-side light passages; and the tray has a two-directional symmetry.

The tray may otherwise comprise cylindrical tray upper and lower portions which have substantially equal diameters and a square column-like tray middle portion provided between these cylindrical tray upper and lower portions and not protruding outward from the circumferential edges of the cylindrical tray upper and lower portions; the cylindrical tray upper portion being provided at the top thereof with a holding part in a concave shape, and being provided in the holding part with two tray-side light passages used for the measurement of light; and the tray has a two-directional symmetry.

In the trays according to these embodiments, the square column-like tray upper portion, tray lower portion or tray middle portion may preferably be worked to have four rounded corners so that the trays are smoothly engageable with the guide provided at the measuring section.

The tray having the two-directional symmetry may alternatively have the following structure.

That is, the tray may comprise a cylindrical tray main body and a pair of planar portions formed by cutting two upper portions of the periphery of the tray main body in parallel to each other; the tray main body is provided at the top thereof with a holding part in a concave shape, is provided in the holding part with two tray-side light passages; and the tray has a two-directional symmetry;

the tray may comprise a cylindrical tray main body and a pair of planar portions formed by cutting two lower portions of the periphery of the tray main body in parallel to each other; the tray main body being provided at the top thereof with a holding part in a concave shape, and being provided in the holding part with two tray-side light passages; and the tray has a two-directional symmetry; or the tray may comprise a cylindrical tray main body and a pair of planar portions formed by cutting two middle portions of the periphery of the tray main body in parallel to each other; the tray main body being provided at the top thereof with a holding part in a concave shape, and being provided in the holding part with two tray-side light passages; and the tray has a two-directional symmetry.

In the trays according to all the foregoing embodiments, at least one linear recession having two-directional symmetry may preferably be provided in the bottom of the tray side portion or the tray main body, and also the tray-side light passages may each preferably have a transverse cross-sectional shape set to have an elliptic shape that is relatively longer with respect to the tray delivery direction. In the former case, the linear recession may be used as the component member of the leakage light preventing means previously described. In the latter case, the tray-side light passages and the measurement-side light passages can stand positionally adjusted to each other for a longer time, and hence the measurement of the taste characteristics can be made higher in speed and can be improved in precision.

Incidentally, in the case of the tray whose opening ends at the tray-side light passages have round or substantially round (including elliptic) cross-sectional shapes, there is a possibility that measurement errors slightly occur depending on the conditions under which the light incidence timing control means previously described is provided.

Figure 38A:
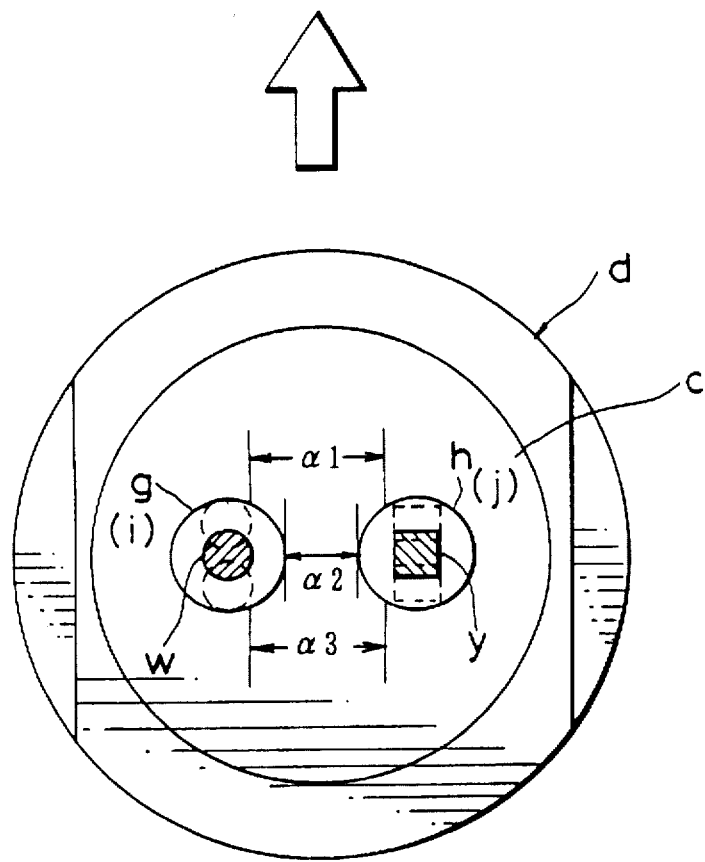
FIG. 38A is a schematic plan view illustrating a state where a tray having a circular cross-sectional shape at its opening ends of the tray-side light passages is delivered over the measuring section.

More specifically, the light is made incident on the vegetable or fruit placed on the tray through one measurement-side light passage i of the measuring section and through one tray-side light passage g of the tray as shown in FIG. 38A. This will be described in greater detail. Laser light is first emitted in the form of a spot in a cross-sectional view, from an end face of an optical fiber w provided in the measurement-side light passage i. This laser light is led into the tray-side light passage g positionally adjusted to the measurement-side light passage i, and thereafter becomes incident on the vegetable or fruit through the tray-side light passage g at its opening end coming into contact with the vegetable or fruit. Meanwhile, the laser light having entered the vegetable or fruit is diffused inside the vegetable or fruit, and becomes emergent from the vegetable or fruit. The light emergent therefrom is led into a tray-side light passage h whose opening end is brought into contact with the vegetable or fruit, and also made to enter a detector y through a measurement-side light passage j. The optical fiber w and the detector y each have a size set smaller than the opening area of the tray-side light passage and measurement-side light passage taking account of rocking motion or the like of a tray d for the measurement of taste characteristics.

The light from the end face of the optical fiber is so designed as to be emitted therefrom at the time the opening ends of the tray-side light passages have come into positional agreement with the opening ends of the measurement-side light passages by means of the light incidence timing control means. Taking account of any slight positional aberration, the emission is usually so controlled that the emission is started immediately before the opening ends come into the positional agreement and is continued until such positional agreement is taken away.

Figure 38B:
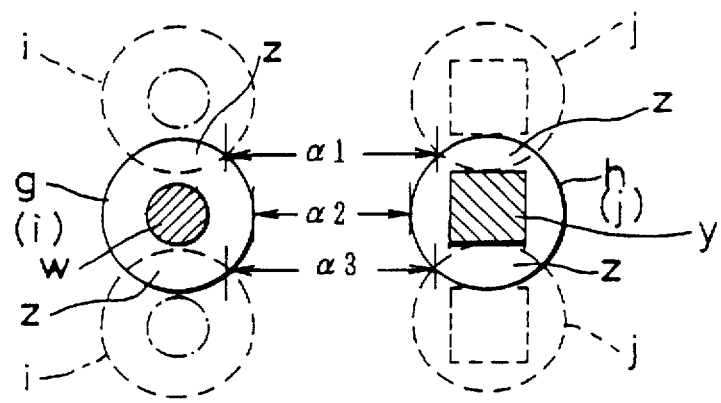
FIG. 38B illustrates a pair of overlapping open areas formed when the opening ends overlap each other which are those of tray-side light passages and measurement-side light passages of the tray during its delivery.

Hence, in the emission of light immediately before the opening ends of the tray-side light passages g and h and the opening ends of the measurement-side light passages i and j come into the positional agreement, the crossing edges of the respective opening ends on the side where a pair of overlapping open areas z face each other which are formed when the opening ends overlap each other as shown in FIG. 38B by upper-side broken lines and middle-part solid lines, stand outward to the inside edges of the respective opening ends (i.e., on the side of each guide on which the tray d is guided). Accordingly, in respect of the overlapping open areas z, a distance α1 between edges on the side where they face each other becomes larger, so that the light path of the laser light emitted from the end face of the optical fiber w and reaching the detector y becomes longer, and correspondingly thereto the amount of light emergent from the vegetable or fruit M and led into the tray-side light passage h becomes smaller.

On the other hand, in the emission of light at the time when the opening ends of the tray-side light passages g and h and the opening ends of the measurement-side light passages i and j come into complete positional agreement, the edges of the overlapping open areas formed when the respective opening ends overlap each other as shown in FIG. 38B by middle-part solid lines come into agreement with the edges of the respective opening ends. Accordingly, in respect of the above overlapping open areas, as shown in FIG. 38B by middle-part solid lines, a distance α2 between edges on the side where they face each other is smallest, so that the above light path becomes shorter and the amount of light emergent from the vegetable or fruit and led into the tray-side light passage h becomes larger.

In the emission of light immediately before the positional agreement between the opening ends of the tray-side light passages g and h and the opening ends of the measurement-side light passages i and j is taken away, like the case immediately before the respective opening ends come into agreement, a distance α3 between edges on the side where the overlapping open areas z face each other becomes larger as shown in FIG. 38B by middle-part solid lines and lower-part broken lines, so that the above light path becomes longer and the amount of light emergent from the vegetable or fruit and led into the tray-side light passage h becomes smaller.

In this way, in the embodiment where the tray whose opening ends at the tray-side light passages have round cross-sectional shapes or the like is used, the amount of light emergent from the vegetable or fruit and entering the detector y varies in accordance with the progress of movement of the tray delivered on the measuring section. Hence, there is a possibility that measurement errors are caused if the taste characteristics such as sugar content of the vegetable or fruit are determined using the data from the detector as they are.

Figure 21A:
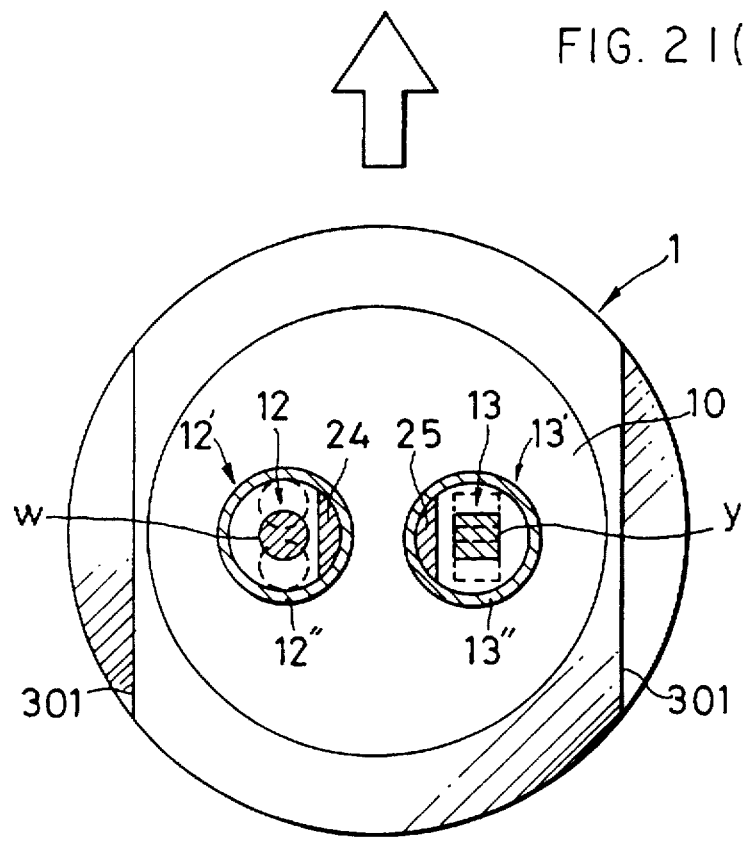
FIG. 21A is a plan view of the tray according to Example 9.

Now, in order to prevent such measurement errors, as shown, for example, in FIG. 21A, the shapes of the opening edges of the tray-side light passages on the side where they face each other and the vegetable or fruit is placed may be set to be shapes with straight lines which are parallel to each other and also parallel to the tray delivery direction.

More specifically, in the embodiment where the shapes of the opening ends of the tray-side light passages on the side where they face each other and the vegetable or fruit is placed are set to be shapes with straight lines which are parallel to each other and also parallel to the tray delivery direction, the inside edges of the overlapping open areas formed when the respective opening ends of the tray-side light passages and measurement-side light passages overlap each other (i.e., edges on the side where a pair of overlapping open areas face each other) substantially come into agreement with the inside edges of opening ends of the tray-side light passages (i.e., the opening edges with straight lines, of the tray-side light passages on the side where they face each other). Accordingly, in respect of the overlapping open areas, the distance between edges on the side where they face each other becomes substantially constant without regard to the progress of movement of the tray, in the course immediately before the opening ends of the tray-side light passages and the opening ends of the measurement-side light passages come into the positional agreement and until such positional agreement is taken away. Thus, in that course, the light path of the laser light emitted from the end face of the optical fiber and reaching the detector can be kept substantially constant, so that it becomes possible to prevent the phenomenon that the amount of light emergent from the vegetable or fruit and entering the detector varies in accordance with the progress of movement of the tray.

The tray having the four-directional symmetry is characterized in that it has a cylindrical tray lower portion and a square column-like tray upper portion projecting upward from the cylindrical tray lower portion and not protruding outward from the circumferential edge of the cylindrical tray lower portion; the square column-like tray upper portion being provided at the top thereof with a holding part in a concave shape, and being provided in the holding part with four tray-side light passages; and the tray has a four-directional symmetry.

Like the tray having a two-directional symmetry as previously described, the tray may alternatively have a structure wherein the cylindrical tray lower portion and the square column-like tray upper portion are inversed, or a structure wherein a square column-like tray middle portion is provided between the cylindrical tray lower and upper portions.

More specifically, the tray may comprise a cylindrical tray upper portion and a square column-like tray lower portion projecting downward from the cylindrical tray upper portion and not protruding outward from the circumferential edge of the cylindrical tray upper portion; the cylindrical tray upper portion being provided at the top thereof with a holding part in a concave shape, and being provided in the holding part with four tray-side light passages; and the tray has a four-directional symmetry.

The tray may otherwise comprise cylindrical tray upper and lower portions which have substantially equal diameters and a square column-like tray middle portion provided between these cylindrical tray upper and lower portions and not protruding outward from the circumferential edges of the cylindrical tray upper and lower portions; the cylindrical tray upper portion being provided at the top thereof with a holding part in a concave shape, and being provided in the holding part with four tray-side light passages; and the tray has a four-directional symmetry.

In the foregoing embodiments, like the tray having a two-directional symmetry, the square column-like tray upper portion, tray lower portion or tray middle portion may preferably be worked to have four rounded corners so that the trays are smoothly engageable with the guide provided at the measuring section. At least two linear recessions having a four-directional symmetry may also be provided in the bottom of the tray lower portion.

In the tray having a four-directional symmetry, the disposition of the four tray-side light passages provided in the holding part and the tray delivery direction may be so designed that a quadrangle formed by connecting the centers of opening ends of the respective tray-side light passages on the side where the vegetable or fruit is placed is in the form of a regular square, and the tray delivery direction is set in the direction of each side of this regular square, or that a quadrangle formed by connecting the centers of opening ends of the respective tray-side light passages on the side where the vegetable or fruit is placed is in the form of a regular square and also the tray delivery direction is set in the direction of diagonals of this regular square.

In order to prevent the measurement errors caused by the light incidence timing control means, the following measures may be taken for the same reasons as in the tray having a two-directional symmetry: In the embodiment where the tray delivery direction is set in the direction of each side of the regular square formed by connecting the centers of opening ends of the respective tray-side light passages on the side where the vegetable or fruit is placed, the shapes of the opening edges of the tray-side light passages on the side where they are adjacent to each other may be set to be shapes with straight lines which are parallel to each other and also parallel to each side of the quadrangle formed by connecting the centers of opening ends of the respective tray-side light passages. In the embodiment where the tray delivery direction is set in the direction of diagonals of the regular square formed by connecting the centers of opening ends of the respective tray-side light passages on the side where the vegetable or fruit is placed, the shapes of the opening edges diagonally confronting each other, of two sets of tray-side light passages and on the side where they face each other may be set to be shapes with straight lines which are parallel to each other and perpendicular to the direction of the diagonals.

When the taste characteristics such as sugar content of vegetables and fruits are measured by the non-destructive taste characteristics measuring apparatus in which any of the above trays of various types is applied, the measurement may preferably be made using light rays having three kinds of wavelengths. One of the three kinds of wavelengths is set within the range of from 900 nm to 920 nm, which are the absorption wavelengths assigned to the sugar. As for other two wavelengths, they are selected from wavelengths of from 860 nm to 890 nm and wavelengths of from 920 nm to 960 nm (provided that 920 nm is excluded), which have nothing to do with the light absorption in sugar. Since the light with wavelengths selected in this way is used, the effect of backgrounds having a wavelength dependence can be accurately removed from the absorption of the light having the above wavelengths of from 900 nm to 920 nm, so that the taste characteristics such as sugar content can be accurately determined. In the case when the light rays having three kinds of wavelengths are used, the non-destructive taste characteristics measuring apparatus is constituted in the manner that three measuring sections are provided in the course of the transport path and the light rays having any kinds of wavelengths are successively made incident on vegetables and fruits in the respective measuring sections to measure their taste characteristics.

Incidentally, when trays on which the measurement objects vegetables and fruits are placed are delivered to the respective measuring sections, the trays are delivered to the measuring sections while being guided by the guide previously described, where some gaps are provided between the trays and the guide taking account of transport stability or the like. Hence, irrespective of the guiding action of the guide, the trays are delivered while rocking in the direction perpendicularly crossing their delivery direction. Then, in the case when the trays are delivered to the measuring sections while rocking, there is a possibility that measurement errors occur for the following reasons even though the light rays having three kinds of wavelengths are used.

Figure 39:
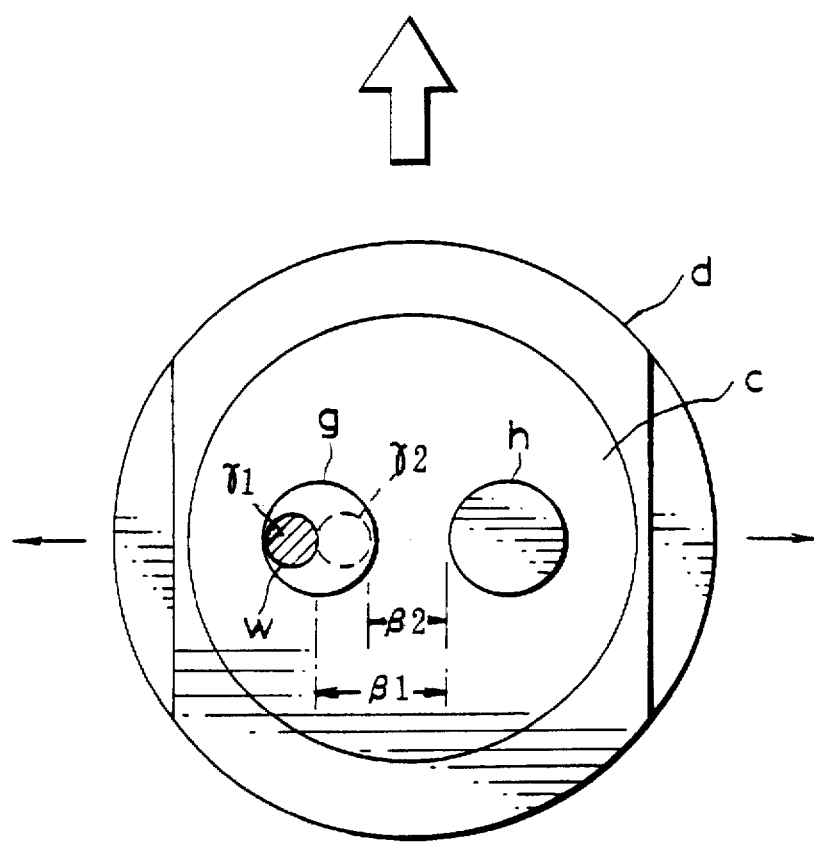
FIG. 39 illustrates a change in the length of light path, caused by rocking of trays, in respect of the light made incident and reaching the detector.

As previously described, the light is made incident on vegetables and fruits through one tray-side light passage and one measurement-side light passage. First, this will be described in greater detail. As shown in FIG. 39, laser light is emitted in the form of a spot in a cross-sectional view, from an end face of an optical fiber w provided in the measurement-side light passage. This laser light is led into the tray-side light passage g. This laser light becomes incident on the vegetable or fruit through the tray-side light passage g. Meanwhile, the laser light having entered the vegetable or fruit is diffused inside the vegetable or fruit, and becomes emergent from the vegetable or fruit. The light emergent therefrom is led into a tray-side light passage h whose opening end is brought into contact with the vegetable or fruit, and also made to enter a detector (not shown) through the measurement-side light passage. Now, when a tray d reaches the measuring section while rocking rightward with respect to its delivery direction (shown by an upward arrow) as shown in FIG. 39, the end face of the optical fiber w is relatively positioned on the left one side (shown by γ1 in FIG. 39) of the tray-side light passage g. Accordingly, a distance β1 between the position of the end face of the optical fiber w and the position of the opening edge of the tray-side light passage h becomes larger, so that the light path of the laser light emitted from the end face of the optical fiber w and reaching the detector becomes relatively longer. As the result, correspondingly thereto, the amount of light emergent from the vegetable or fruit and led into the tray-side light passage h becomes smaller. On the other hand, when the tray d reaches the measuring section while rocking leftward with respect to its delivery direction as shown in FIG. 39, the end face of the optical fiber w is relatively positioned on the right one side (shown by γ2 in FIG. 39) of the tray-side light passage g. Accordingly, a distance β2 between the position of the end face of the optical fiber w and the position of the opening edge of the tray-side light passage h becomes smaller, so that the above light path becomes relatively shorter. As the result, correspondingly thereto, the amount of light emergent from the vegetable or fruit and led into the tray-side light passage h becomes larger.

Hence, when these detection light rays obtained in the three measuring sections are used to determine the taste characteristics such as sugar content of the vegetable or fruit, measurement errors may occur because of the rocking of trays. Also, such rocking of trays causes delicate changes in the positions at which the light is incident on the vegetable or fruit, so that the light rays having three wavelengths as described above may pass through different regions of the vegetable or fruit and becomes emergent from the vegetable or fruit. Thus, such changes may also cause measurement errors. Especially when the measurement objects are vegetables and fruits such as muskmelons and pumpkins, which may have greatly different surface shapes and patterns at some portions thereof, the reflectance may greatly change depending on where the light is incident thereon.

In such a case, a tray delivery position control means may preferably be provided in each measuring section provided in the course of the transport path. More specifically, this tray delivery position control means is a means for controlling the delivery position of the tray while bringing the reference surface of the tray into engagement with a guide face provided in the tray delivery direction, and is distinguished from the guide previously described, in view of various specific constitutions as described below.

Figure 24:
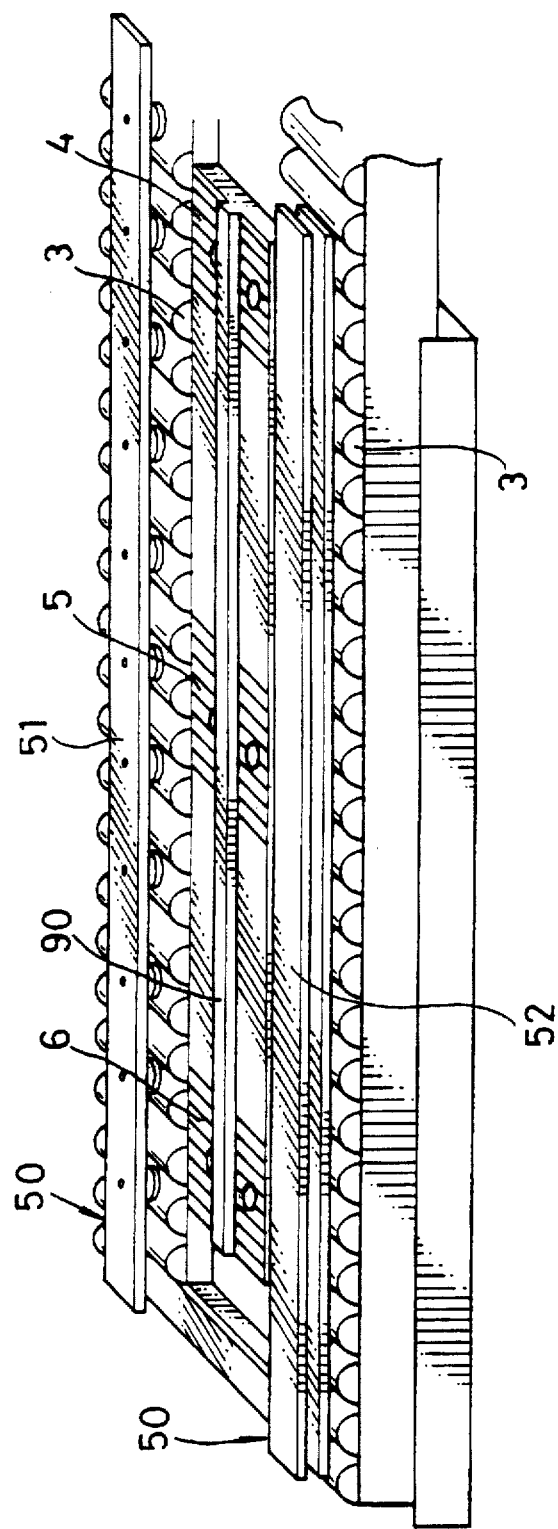
FIG. 24 is a perspective illustration of the main part of a non-destructive taste characteristics measuring apparatus according to Example 12.

This tray delivery position control means can have a variety of specific constitutions. For example, as shown in FIG. 24, etc. it may comprise a pair of side bars provided at an appropriate interval on both side edges of the transport path at each measuring section, and a pressing means fixed to one of the side bars and pressing a tray to be delivered between the side bars, against the other side bar to bring the reference surface of the tray into engagement with a guide face of the latter's side bar.

In another embodiment, the tray delivery position control means may comprise a pair of side bars provided at an appropriate interval on both side edges of the transport path at each measuring section, and a pressing means fixed to a tray to be delivered between the side bars and pressing one of the side bars to exert a counterforce to bring the reference surface of the tray into engagement with a guide face of the other side bar.

In still another embodiment, the tray delivery position control means may comprise a delivery belt provided on one side edge of the transport path at each measuring section so as to have the function as the guide face and be brought into contact with the reference surface of a tray, to deliver the tray, a side bar provided on the other side edge of the transport path and at a portion facing the delivery belt, and a pressing means fixed to the side bar, for bringing the reference surface of the tray to be delivered between the side bars, into contact with a guide face of the delivery belt.

In these tray delivery position control means, a plurality of rollers may be provided at one of contacting surfaces where the side bars and the tray come into contact, so as to decrease the frictional force accompanying the contact.

In the embodiment where the rollers are provided as described above, the pressing means may comprise a resilient material layer formed of rubber or urethane resin provided on the periphery of each roller. The pressing means may alternatively comprise a supporting means for movably supporting the axis of each roller, and a spring means for pressing the support means to push out the periphery of the roller against the contact surface side of the side bar or tray.

Still alternatively, the tray delivery position control means may be made up using a pair of delivery belts. More specifically, the tray delivery position control means may comprise a first delivery belt provided on one side edge of the transport path at each measuring section so as to have the function as the guide face and be brought into contact with the reference surface of a tray, to deliver the tray, a second delivery belt provided on the other side edge of the transport path and at a portion facing the first delivery belt, and a pressing means provided on the second delivery belt, for bringing the reference surface of the tray to be delivered between the first delivery belt and the second delivery belt, into contact with a guide face of the first delivery belt.

In the embodiment where the tray delivery position control means is provided at each measuring section of the non-destructive taste characteristics measuring apparatus according to the present invention, the measurement objects vegetables and fruits can be transported to the proper position of the measuring section without causing the rocking motion of the trays on which the vegetables and fruits are placed. Accordingly, the light path of the emitted laser light reaching the detector may less change in length and also light rays having different wavelengths can be successively made incident on the vegetable or fruit at substantially the same position thereof, so that the differences in reflectance of the respective light rays can be minimized. Also, the information of light can be obtained at substantially the same position inside the vegetable or fruit, and hence the measurement errors can be decreased.

The non-destructive taste characteristics measuring apparatus of the present invention can measure both sugar content and ripeness of vegetables and fruits such as muskmelons, watermelons and pumpkins. More specifically, when the light is incident on a fruit such as a muskmelon and the light emergent from the fruit is measured, its sugar content and ripeness can be both selectively determined in accordance with differences in methods for processing the measured data.

As described above, according to the non-destructive taste characteristics measuring apparatus of the present invention, the light is incident on the vegetable or fruit through one measurement-side light passage of the measuring section and through one tray-side light passage provided in the holding part of the tray and the light emergent from the vegetable or fruit enters the detector through the other tray-side light passage also provided in the holding part of the tray and through the other measurement-side light passage of the measuring section. Hence the light can be prevented from leaking when the light is incident and enter the detector. Thus, the light can be passed into the vegetable or fruit in a good efficiency and also the light emergent from the vegetable or fruit can enter the detector in a good efficiency.

Accordingly, it can be effectively done to properly and highly precisely measure the sugar content and so forth of vegetables and fruits without increasing the power of the light made incident on the vegetables and fruits.

Since also the tray-side light passages, which correspond to the conventional tubular members, are provided in the holding part of the tray, it is unnecessary to provide any moving mechanism for the tubular members which otherwise must be moved in synchronization with the transport of vegetables and fruits, so that the sugar content and so forth can be measured at a high speed and a high precision without complicating the structure of the measuring apparatus.

According to the tray of the present invention, the tray has a two-directional symmetry or four-directional symmetry on the whole. Hence, when trays are delivered into the transport path, they can be delivered without taking care of the directions of trays with respect to their delivery direction. Also, the tray has the structure wherein the corners of the tray do not protrude outward from the circumferential edge of the cylindrical tray, and hence it can be delivered in a good performance when delivered through the transport path at its part other than the measuring section. Still also, the tray has flat surfaces serving as reference surfaces on its periphery, and hence accurate positional control can be made when delivered through the measuring section provided in the course of the transport path.

EXAMPLES

The present invention will be described below in greater detail by giving Examples and with reference to the accompanying drawings.

Example 1

Figure 3:
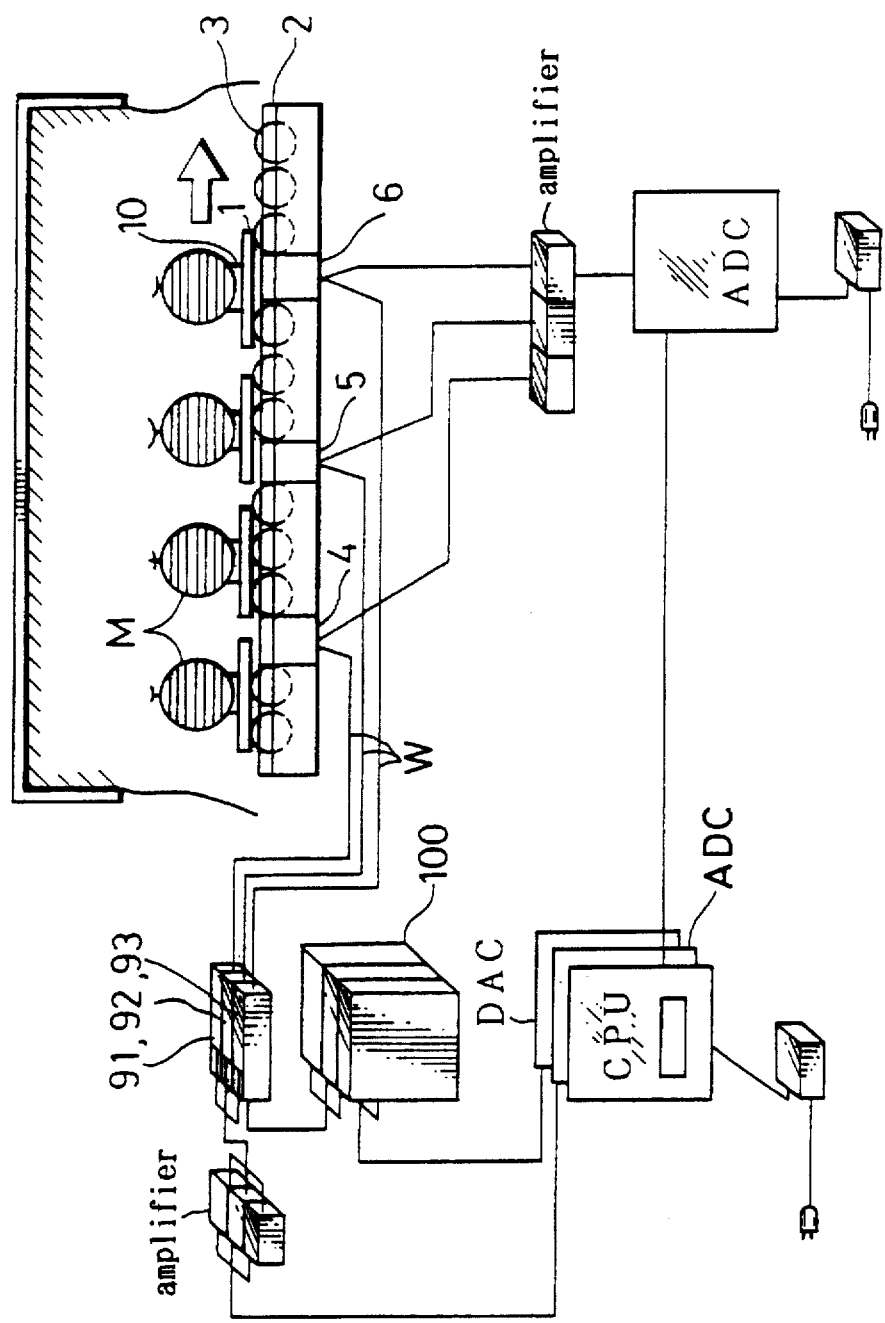
FIG. 3 is an illustration of the whole construction of the non-destructive taste characteristics measuring apparatus according to Example 1.

As shown in FIGS. 1 to 3, a non-destructive taste characteristics measuring apparatus according to the present Example is constituted chiefly of a plurality of trays 1 each having a holding part 10 on which vegetables and fruits (muskmelons) M are individually placed; a pair of guides 2 that guide the trays along the transport path; a roller conveyor 3 serving as a tray delivery means that moves the trays 1 at a speed of, e.g., 60 cm/second; three box-like measuring sections 4, 5 and 6 provided in the transport path at appropriate intervals; a vegetable or fruit presence-absence sensor 7 provided in the vicinity of each measuring section to judge the presence or absence of the vegetables and fruits (muskmelons) M on the trays 1; a position sensor 8 similarly provided in the vicinity of each measuring section to detect a detectee member 11 provided to each tray 1, to find out the points of time at which the trays 1 and the measuring sections 4, 5 and 6 come into positional agreement; three semiconductor lasers 91, 92 and 93 that emit light to the muskmelons M at the respective measuring sections 4, 5 and 6; and detectors (not shown) which light rays emergent from the muskmelons M enter at the respective measuring sections 4, 5 and 6. The roller conveyer may be comprised of a belt conveyor.

The trays 1 are each comprised of rectangular plate materials as shown in FIG. 1 or 2. At its substantially central part, a substantially circular holding part 10 on which a muskmelon M is placed is integrally provided. In this holding part 10, two tray-side light passages 12 and 13 are provided one opening ends of which are so made as to come in contact with the lower periphery of the vegetable or fruit and the other opening ends of which stand open outward at the bottom of the tray 1. A linear recession 14 that can be slidably loosely fitted to a linear projection 90 provided on the top of the measuring section 4 is also provided in the bottom of the tray at its substantially middle portion. On both sides of the tray 1, a pair of engaging rollers 15 are provided which respectively engage with the guides 2, and the detectee member 11 is fixedly positioned between the engaging rollers 15 on one side.

Meanwhile, in the measuring section 4, the linear projection 90 is provided at the middle portion on its top side, and measurement-side light passages 41 and 42 are also provided which are comprised of two tubular members and positionally adjustable to the tray-side light passages 12 and 23. Also, optical fibers w that transmit laser light emitted from the semiconductor lasers 91, 92 and 93 are provided at opening ends of one measurement-side light passage 41 of the passages 41 and 42. (In the measuring section 4, an optical fiber w that transmits laser light emitted from the semiconductor laser 91 is provided. Similarly, in other measuring sections, optical fibers w that transmit laser light emitted from the semiconductor lasers 92 and 93 are respectively provided; see FIG. 3). A detector (not shown) is provided at an opening end of the other measurement-side light passage 42. The linear projection 90 provided on the top side of the measuring section 4 acts to block the gap between the tray 1 and the measuring section 4 as shown in FIG. 2, so that the laser light emitted from the semiconductor laser 91 and passing through the measurement-side light passage 41 is prevented from entering the measurement-side light passage 42. Namely, it acts as the leakage light preventing means. Thus, only the light emergent from the muskmelon M enters the detector (not shown) provided at the opening end of the measurement-side light passage 42, and hence measurement errors caused by the leakage light of the semiconductor laser 91 can be avoided in the measurement of taste characteristics such as sugar content and ripeness of the vegetable or fruit.

Signals of detected information from the vegetable or fruit presence-absence sensor 7 and the sensor 8 are processed so as to be inputted to power sources 100 for the semiconductor lasers 91, 92 and 93. When the signals of detected information from the vegetable or fruit presence-absence sensor 7 are inputted and also signals of detected information from the sensor 8 are inputted, the power sources 100 are actuated and laser light is emitted from the semiconductor lasers 91, 92 and 93 each. When no signals are inputted from the vegetable or fruit presence-absence sensor 7 (i.e., when no fruit M is present on the tray 1) or no signals are inputted from the sensor 8, the power sources 100 are so set as to turn off.

In this non-destructive taste characteristics measuring apparatus, the power sources 100 are switched on at every time when the tray 1 with the fruit M placed thereon passes through the respective measuring sections 4, 5 and 6. In the measuring section 4, laser light of 930 nm is emitted for 20 milliseconds. This laser light is made incident on the fruit M though the measurement-side light passage 41 and the tray-side light passage 12 and then the light emergent from the fruit M enters the detector (not shown) through the tray-side light passage 13 and the measurement-side light passage 42. Similarly, subsequently in the measuring section 5, laser light of 910 nm is emitted for 20 milliseconds, and, in the measuring section 6, laser light of 880 nm is emitted for 20 milliseconds. Each light emergent from the fruit M enters each detector (not shown), and the taste characteristics of the fruit M is measured. As shown in FIG. 3, the apparatus is so designed that these are measured in a dark room.

In the non-destructive taste characteristics measuring apparatus according to the present Example, the laser light is incident on the fruit M through the measurement-side light passage 41 of the measuring section 4 positioned at the part facing the bottom side of the tray 1 in the transport path and through the tray-side light passage 12 provided in the holding part 10 of the tray 1 with the fruit M placed thereon, and the light emergent from the fruit M enters the detector through the other tray-side light passage 13 provided in the holding part 10 of the tray 1 and also through the other measurement-side light passage 42 of the measuring section 4. Hence the light can be prevented from leaking when the light is incident on the fruit M and enter the detector, the light can be passed into the fruit M in a good efficiency, and also the light emergent from the fruit M can enter the detector in a good efficiency.

Thus, the apparatus has the advantage that the taste characteristics such as sugar content and ripeness of the fruit M can be properly and highly precisely measured without increasing the power of the light made incident on the fruit M.

The distance between the measurement object fruit M and the detector (not shown) fixedly provided at the opening end of the measurement-side light passage 42 may delicately change depending on the differences in size of fruits M successively placed on the holding part 10 of the tray 1. Accordingly, with variations of this distance, the amount of the light entering the detector also varies because of absorption of light in the inner walls of the tray-side light passage 13 and measurement-side light passage 42, so that measurement precision may become non-uniform because of the difference in size of vegetables and fruits.

Now, changes in intensity of the detection light entering the detector which accompany the variations in the distance were measured using an apparatus which is a modification of the present Example, whose tray-side light passages 12 and 13 and measurement-side light passages 41 and 42 were gold-plated on their inner walls, and using an apparatus (a comparative example) in which the corresponding inner walls were blacked by anodizing treatment.

Figure 4:
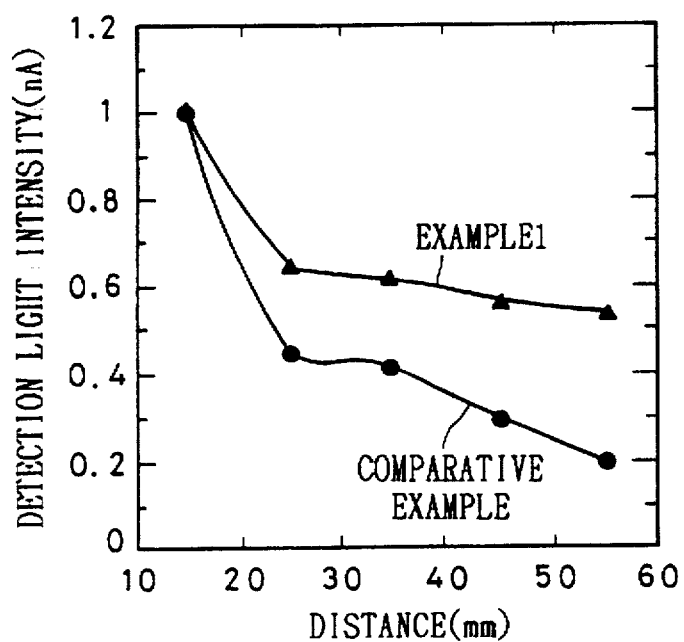
FIG. 4 is a graph showing the relationship between i) variations in distance between a detector and vegetables and fruits ii) and changes in detection light intensity, in respect of a modification of the non-destructive taste characteristics measuring apparatus according to Example 1 and a comparative apparatus.

The results are shown by a graph in FIG. 4. From the results shown in the graph, it has been confirmed that, while in the comparative apparatus the intensity of detection light decreases with an increase in the distance between the fruit M and the detector, its variations are relatively small in the apparatus according to a modification of the apparatus of the present Example.

In the present Example, the detector is constituted of a plurality of detector elements in combination. This is so designed that all the detection light emergent from vegetables and fruits can be received by the respective detector elements of the detector to thereby increase detection precision. It, however, is optional to make up the detector using a plurality of detector elements or using a single detector element.

Example 2

Figure 5:
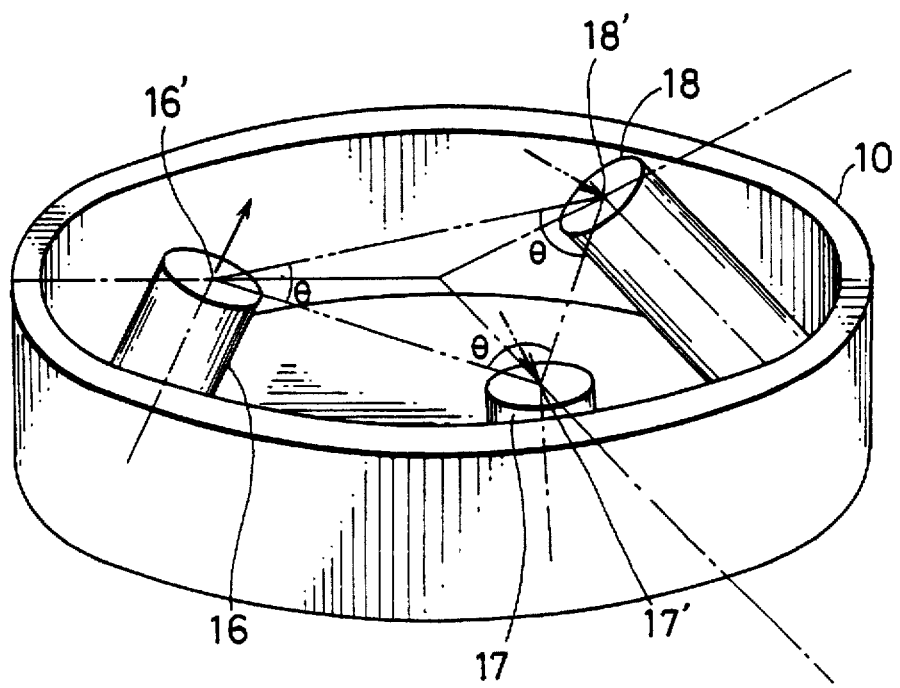
FIG. 5 is a perspective illustration of the holding part of a non-destructive taste characteristics measuring apparatus according to Example 2.
Figure 6:
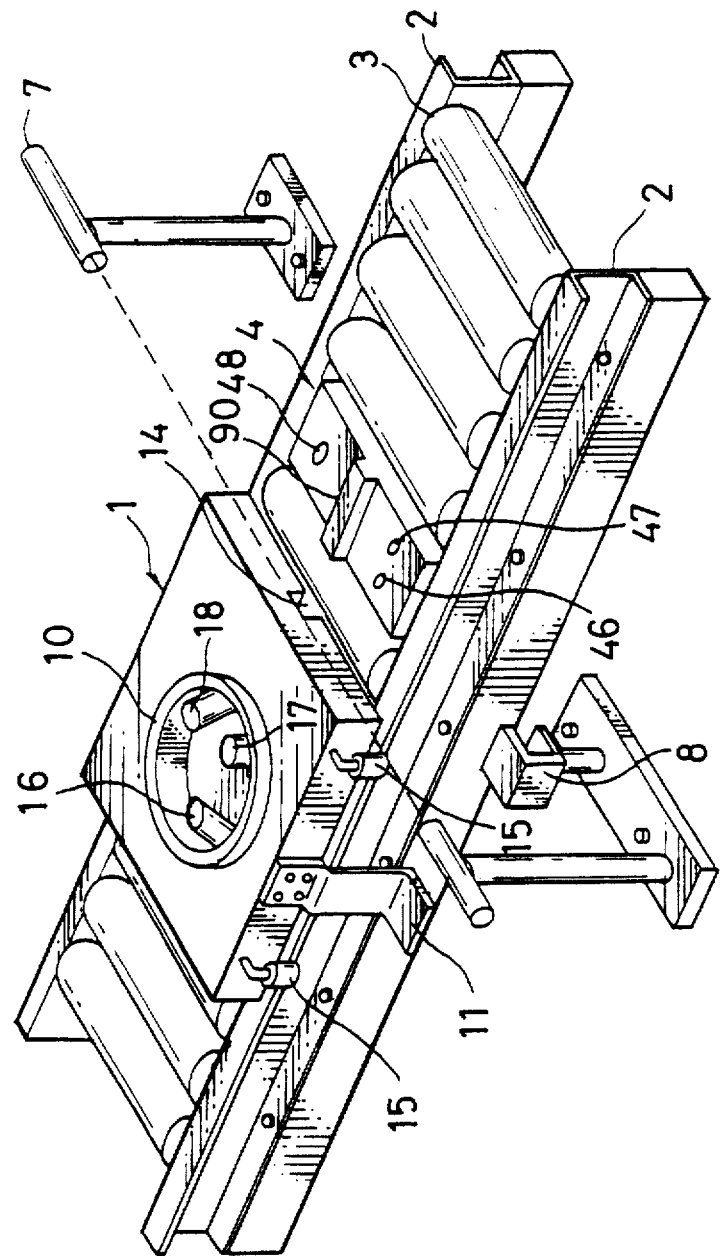
FIG. 6 is a perspective illustration of the main part of the non-destructive taste characteristics measuring apparatus according to Example 2.

A non-destructive taste characteristics measuring apparatus according to the present Example is substantially the same as the non-destructive taste characteristics measuring apparatus according to Example 1 except that, as shown in FIGS. 5 and 6, the tray has a different structure, the number of the tray-side light passages provided in the holding part 10 is increased by one to provide three light passages, and corresponding to the number of the tray-side light passages the number of the measurement-side light passages has also increased by one to provide three light passages.

As shown in FIGS. 5 and 6, the tray 1 is comprised of a rectangular plate material and a circular opening is provided at substantially the center thereof. In this opening, a cylindrical holding part 10 is set, and tray-side light passages 16, 17 and 18 formed of three tubular members are provided in this cylindrical holding part 10. In substantially the middle of the bottom of the tray 1, a linear recession 14 is provided to which a linear projection 90 provided on the top of the measuring section 4 can be slidably loosely fitted. The tray-side light passages 16, 17 and 18 may be provided in such a dispositional relationship that a triangle formed by connecting the centers 16', 17' and 18' of the opening ends of the tray-side light passages 16, 17 and 18 on the side opposite to the measuring section is a regular triangle (i.e., the angles indicated by θ in FIG. 5 are 60 degrees). However, this dispositional relationship of the tray-side light passages 16, 17 and 18 is optional, and the triangle formed by connecting the centers 16', 17' and 18' of the opening ends need not necessarily be a regular triangle, and may of course be set to be an isosceles triangle.

In the measuring section 4, an optical fiber (not shown) that transmits laser light emitted from the semiconductor laser 91 is provided on the other opening end side of a measurement-side light passage 46 positionally adjustable to the opening end of the tray-side light passage 16 at its tray-side opening end. On the opening end side of the remaining two measurement-side light passages 47 and 48, two detectors (not shown) are provided which light rays enter, emitted from the semiconductor laser 91 and separately emergent from the vegetable or fruit.

In the non-destructive taste characteristics measuring apparatus according to the present Example, the vegetable or fruit can be three-point supported by the members constituting the three tray-side light passages 16, 17 and 18. Thus, this apparatus has the advantage that vegetables and fruits can be stably transported.

In the present apparatus, the light rays made to pass into the vegetable or fruit and transmitted through different portions are separately detected by the two detectors, and hence the apparatus has also the advantage that the taste characteristics such as sugar content can be measured in a more improved precision than the case when they are measured using one detector.

Figure 7:
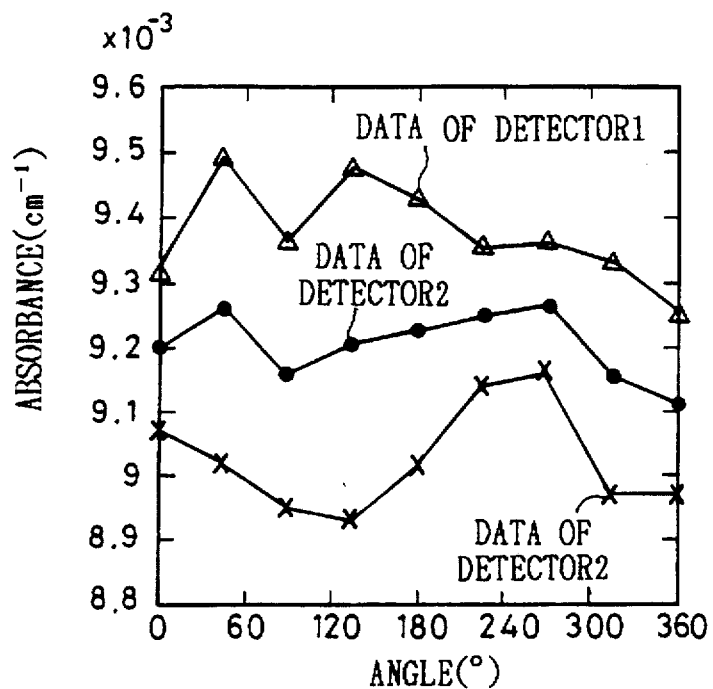
FIG. 7 is a graph showing the relationship between disposition angles (degrees) and light absorbance, the angles being those of vegetables and fruits (muskmelons) to the holding part, in the case when sugar content of the vegetables and fruits was measured using the non-destructive taste characteristics measuring apparatus according to Example 2.
Figure 34:
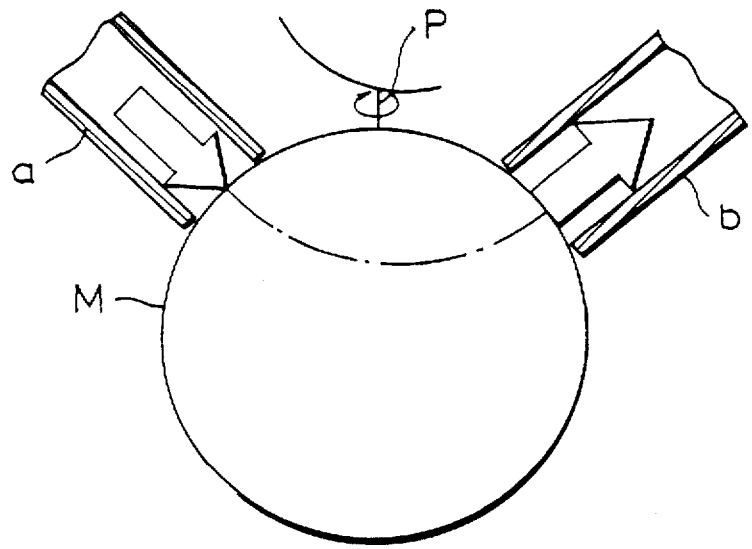
FIG. 34 illustrates the principle of a conventional non-destructive taste characteristics measuring method.

FIG. 7 is a graph showing that in the present Example the taste characteristics can be measured in an improved precision. More specifically, the graph show the relationship between disposition angles (degrees) and light absorbance in the case when sugar content of fruits M was measured in such a state that, when fruits (muskmelons) are placed with their pedicels up on the holding part 10 of the tray 1, the vine or stem p of a fruit (a muskmelon) M as shown in FIG. 34 is set as the rotating shaft and the fruit M is disposed at an angle of 0 degree, 60 degrees, 120 degrees, 180 degrees, 240 degrees, 300 degrees or 360 degrees on the basis of an appropriate portion thereof. In the graph shown in FIG. 7, "data of detector 1" indicates data of absorbance which were obtained according to measurements from the detector (not shown) provided on the opening end side of the measurement-side light passage 47; "data of detector 2", data of absorbance which were obtained according to measurements from the detector (not shown) provided on the opening end side of the measurement-side light passage 48; and "data of Example 2", data of absorbance which are based on average values of the data of detector 1 and data of detector 2.

From the data of Example 2 in this graph, it is confirmed that, in the non-destructive taste characteristics measuring apparatus according to Example 2, the data of absorbance thus obtained are less non-uniform even if the vegetable or fruit (muskmelon) is disposed at any angles with respect to the holding part 10 of the tray 1, and hence the sugar content can be stably measured.

Example 3

Figure 9:
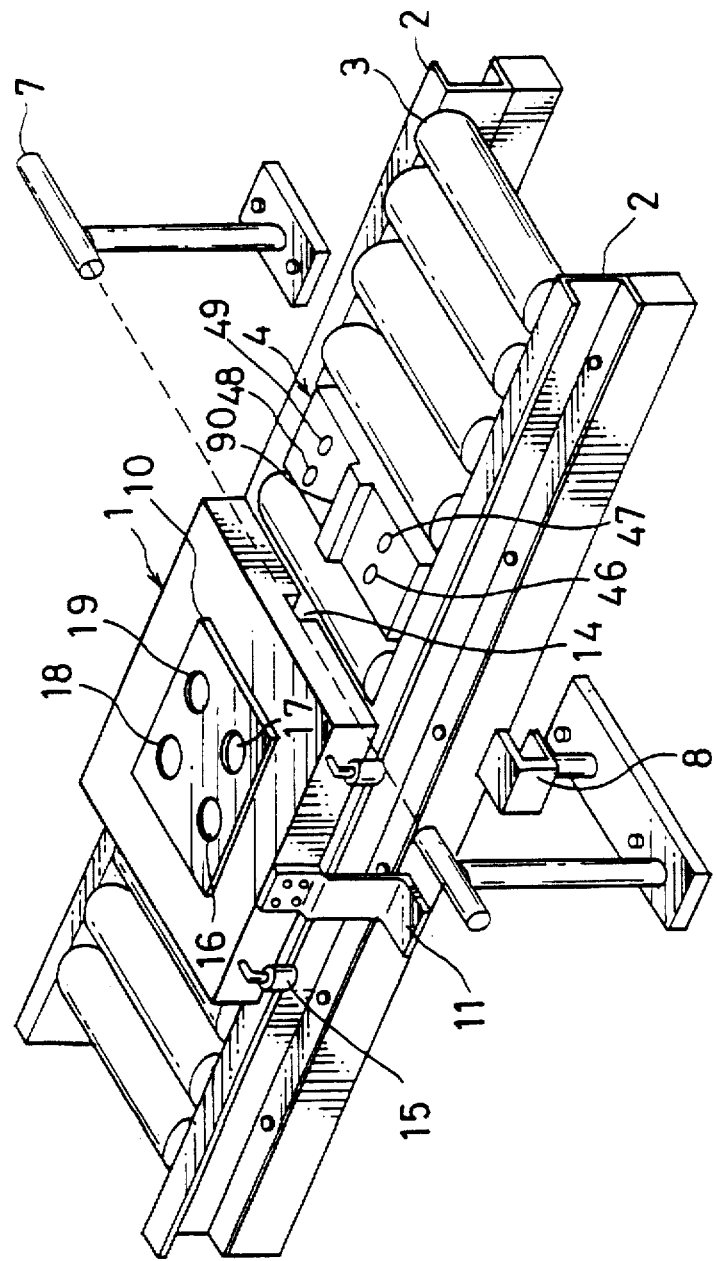
FIG. 9 is a perspective illustration of the main part of a non-destructive taste characteristics measuring apparatus according to Example 3.

A non-destructive taste characteristics measuring apparatus according to the present Example is substantially the same as the non-destructive taste characteristics measuring apparatus according to Example 1 except that, as shown in FIG. 9, the tray has a different structure, the number of the tray-side light passages provided in the holding part 10 is increased by two to provide four light passages, and corresponding to the number of the tray-side light passages the number of the measurement-side light passages has also increased by two to provide four light passages.

As shown in FIG. 9, the tray 1 is comprised of a rectangular plate material and a square opening is provided at substantially the center thereof. In this opening, a square and plate-like holding part 10 is set, and tray-side light passages 16, 17, 18 and 19 are made in this plate-like holding part 10 which are so made as to come into contact with the lower periphery of a vegetable or fruit (not shown) at their one opening ends and stand open outward from the bottom side of the tray 1 at their other opening ends. In substantially the middle of the bottom of the tray 1, the linear recession 14 is provided to which the linear projection 90 provided on the top of the measuring section 4 can be slidably loosely fitted.

The four tray-side light passages 16, 17, 18 and 19 made in the plate-like holding part 10 are so provided as to be symmetrical to each other (i.e., a quadrangle formed by connecting the centers of the respective tray-side light passages is set to be a regular square). Also, in substantially the middle of the tray 1 on the bottom side, two linear recessions (not shown) positionally adjusted to the linear recession 14 provided in the bottom of the tray 1 are formed in the manner they cross each other at right angles. Thus, when the holding part 10 is fitted to the opening of the tray 1, it can be set in proper position if fitted in any directions, i.e., from the front, rear, right or left.

In the measuring section 4, optical fibers (not shown) that transmit laser light emitted from the semiconductor laser 91 are respectively provided on the other opening end side of measurement-side light passages 46 and 47 positionally adjustable to the opening ends of the tray-side light passages 16 and 17 at their tray-side opening ends. On the opening end side of the remaining two measurement-side light passages 48 and 49, two detectors (not shown) are provided which light rays enter, emitted from the semiconductor laser 91 and separately emergent from the vegetable or fruit.

In the present non-destructive taste characteristics measuring apparatus according to Example 3, light rays having the same wavelengths are simultaneously made incident on the vegetable or fruit in the different directions and also the light rays transmitted through different portions of the inside of the vegetable or fruit are separately detected by the two detectors, and hence the apparatus has the advantage that the taste characteristics such as sugar content can be measured in a higher precision than the case when they are measured by the non-destructive taste characteristics measuring apparatus according to Examples 1 and 2.

Figure 8:
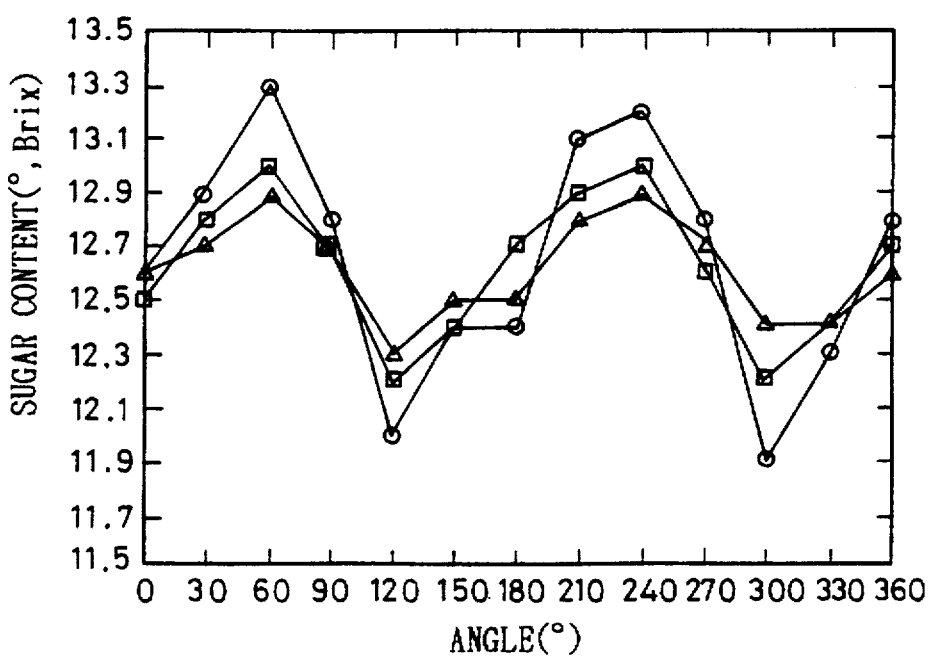
FIG. 8 is a graph showing the relationship between disposition angles (degrees) and sugar content (degrees, Brix), the angles being those of vegetables and fruits to the holding part, in the case when sugar content of the vegetables and fruits was measured using the non-destructive taste characteristics measuring apparatus according to Example 3.

FIG. 8 is a graph showing that in the present Example the taste characteristics can be measured in an improved precision. More specifically, the graph show the relationship between disposition angles (degrees) and sugar content (degrees, Brix) in the case when sugar content of fruits M was measured in such a state that, when fruits (muskmelons) are placed with their pedicels up on the holding part 10 of the tray 1, the vine or stem of a fruit (a muskmelon) is set as the rotating shaft and the fruit is disposed at an angle of from 0 degree to 360 degrees selected at intervals of 30 degrees on the basis of an appropriate portion thereof. In the graph shown in FIG. 7, the solid line with circles indicates data obtained using the non-destructive taste characteristics measuring apparatus according to Example 1 (i.e., incident through one passage/emergent through one passage); the solid line with squares indicates data obtained using the non-destructive taste characteristics measuring apparatus according to Example 2 (i.e., incident through one passage/ emergent through two passages); the solid line with triangles indicates data obtained using the non-destructive taste characteristics measuring apparatus according to the present Example (i.e., incident through two passages/emergent through two passages).

From the data of Example 3 in this graph, it is confirmed that, in the non-destructive taste characteristics measuring apparatus according to Example 3, the data of sugar content (degrees, Brix) thus obtained are less non-uniform (plus-minus 0.3 degree Brix or less) even if the vegetable or fruit (muskmelon) is disposed at any angles with respect to the holding part 10 of the tray 1, and hence the sugar content can be more stably measured than the instances where the non-destructive taste characteristics measuring apparatus according to Examples 1 and 2 are used.

In addition, in the non-destructive taste characteristics measuring apparatus according to the present Example, the four tray-side light passages 16, 17, 18 and 19 made in the plate-like holding part 10 are so provided as to be symmetrical to each other as described above and also, in substantially the middle of the holding part 10 on the bottom side, two linear recessions (not shown) positionally adjusted to the linear recession 14 provided in the bottom of the tray 1 are formed in the manner they cross each other at right angles, and hence, when the holding part 10 is fitted to the opening of the tray 1, it can be set in proper position if fitted in any directions, i.e., from the front, rear, right or left. Thus, the apparatus has the advantage that the degree of freedom in the manner of arrangement of trays can be enhanced when the above plate-like holding part 10 is set in each tray 1 in the transport path.

Example 4

Figure 10:
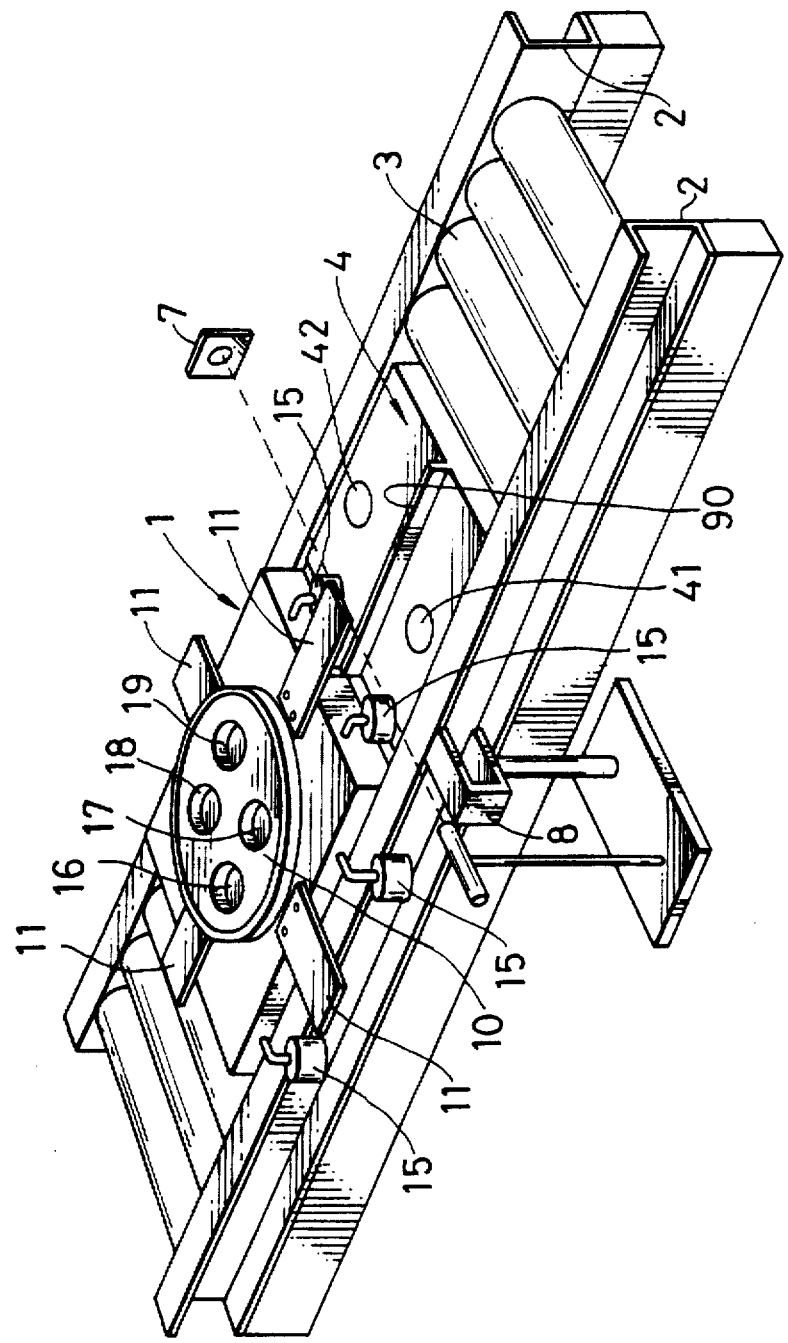
FIG. 10 is a perspective illustration of the main part of a non-destructive taste characteristics measuring apparatus according to Example 4.

A non-destructive taste characteristics measuring apparatus according to the present Example is substantially the same as the non-destructive taste characteristics measuring apparatus according to Example 3 except that, as shown in FIG. 10, the tray has a different structure, the number of the measurement-side light passages provided in the measuring section is changed from four to two.

More specifically, the tray 1 is comprised of a rectangular plate material and a substantially circular holding part 10 on which a vegetable or fruit is placed is integrally provided at substantially the center thereof. In this holding part 10, four tray-side light passages 16, 17, 18 and 19 are made. In substantially the middle of the bottom of the tray 1, two linear recessions to which the linear projection 90 provided on the top of the measuring section 4 can be slidably loosely fitted are provided in the manner they cross each other at right angles. Engaging rollers engageable with a pair of guides 2 and wing-like detectee members are respectively provided on the four sides of the tray 1.

In each measuring section, two measurement-side light passages 41 and 42 successively positionally adjustable to the opening ends of two sets of tray-side light passages 16, 17 and 18, 19 are provided, and an optical fibers (not shown) that transmits laser light emitted from the semiconductor laser is provided in one measurement-side light passage 41 and a detector is provided in the other measurement-side light passage 42.

According to the present non-destructive taste characteristics measuring apparatus, light rays having the same wavelengths are successively made incident on the vegetable or fruit at different timing through the one measurement-side light passage 41 and the two tray-side light passages 16 and 17 successively positionally adjusted thereto, and the light rays emergent from the vegetable or fruit successively enter the detector through the two tray-side light passages 18 and 19 and the other measurement-side light passage 42 positionally adjusted thereto. Hence, the light rays transmitted through different portions of the inside of the vegetable or fruit can be separately detected by one detector. Thus, the apparatus has the advantage that, even though the number of the detector is halved, the taste characteristics such as sugar content can be measured in a high precision as in the case when they are measured by the non-destructive taste characteristics measuring apparatus according to Example 3.

In addition, the tray itself has a four-directional symmetry, and hence the apparatus has the advantage that, when trays with vegetables and fruits placed thereon are delivered in the transport path, they can be delivered without so much taking care of the directions of the trays with respect to their delivery direction.

Example 5

Figure 11:
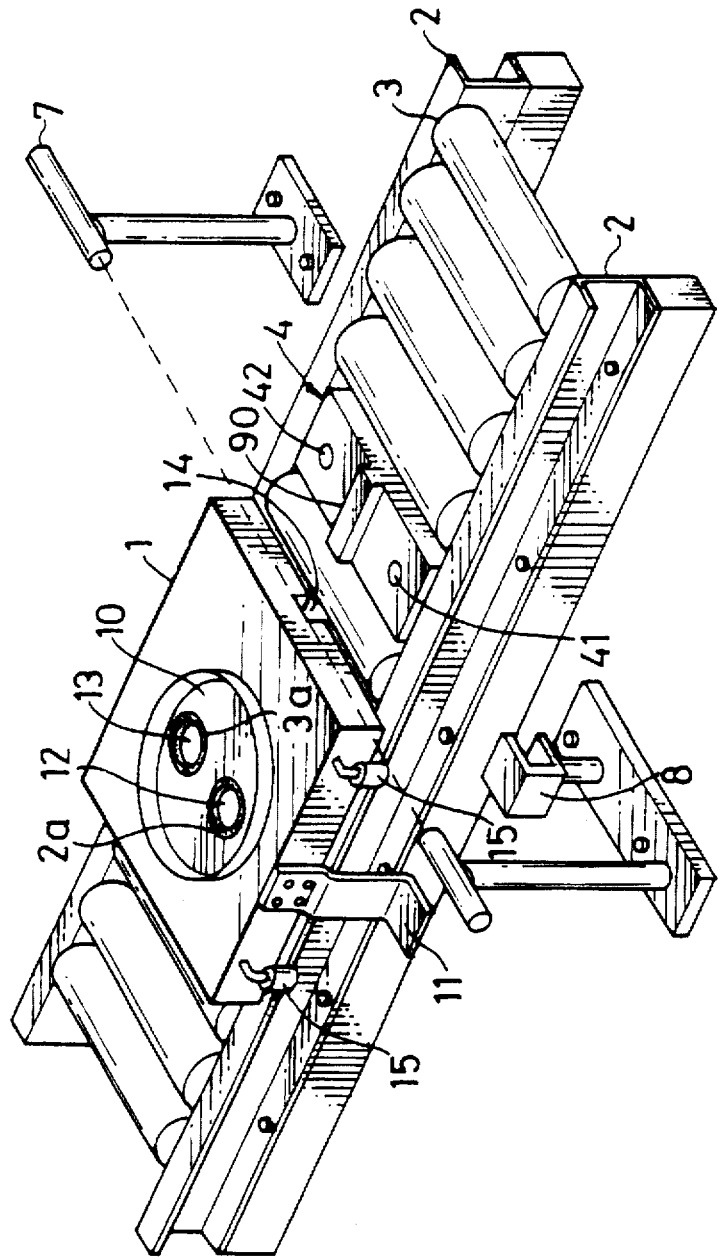
FIG. 11 is a perspective illustration of the main part of a non-destructive taste characteristics measuring apparatus according to Example 5.

A non-destructive taste characteristics measuring apparatus according to the present Example is substantially the same as the non-destructive taste characteristics measuring apparatus according to Example 1 except that, as shown in FIG. 11, ring-like pad members 2a and 3a made of urethane rubber are respectively provided via an adhesive, along edges of the opening ends of the respective tray-side light passages 12 and 13 of the tray 1 on the side where a vegetable or fruit is placed.

In the present non-destructive taste characteristics measuring apparatus, the pad members are deformed by the weight of the vegetable or fruit when it is placed on the tray 10, so that the gaps between the periphery of the vegetable or fruit and the opening ends of the tray-side light passages 12 and 13 are closed by the action of the pad members 2a and 3a. Hence, the measurement errors on the taste characteristics such as sugar content, caused by leakage light can be prevented without regard to the size of the vegetable or fruit.

Thus, the apparatus has the advantage that the taste characteristics such as sugar content can be measured in a higher precision than the case when they are measured by the non-destructive taste characteristics measuring apparatus according to Example 1.

Example 6

The present Example and those up to Example 11 are concerned with trays preferably usable in the non-destructive taste characteristics measuring apparatus according to the present invention.

Figure 12A:
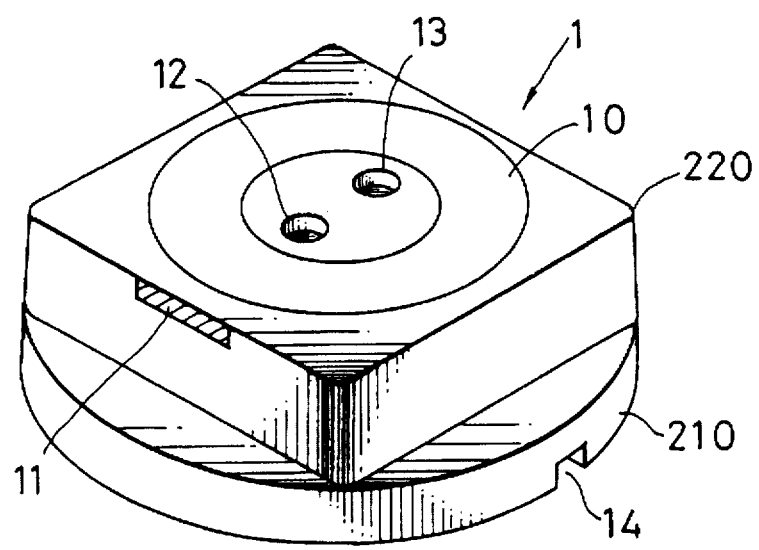
FIG. 12A is a top-side perspective illustration of a tray according to Example 6, and FIG. 12B a bottom-side perspective illustration of the tray.
Figure 12B:
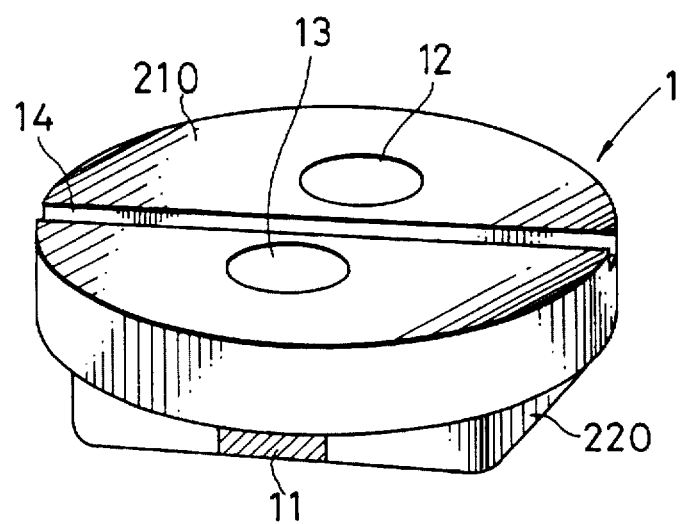

As shown in FIGS. 12A and 12B, the tray according to the present Example as denoted by reference numeral 1 is constituted chiefly of a cylindrical tray lower portion 210 and a substantially square column-like tray upper portion 220 projecting upward from the cylindrical tray lower portion 210 and not protruding outward from the circumferential edge of the cylindrical tray lower portion 210. Also, the tray upper portion 220 is provided in such a manner that its center overlap with the center of the cylindrical tray lower portion 210 so that the tray has a two-directional symmetry.

The tray upper portion 220 is provided at the top thereof with the holding part 10 in a conical concave shape, and is provided in the holding part 10 with two tray-side light passages 12 and 13 at its position having the two-directional symmetry. Also, the square column-like tray upper portion 220 is worked to have four rounded corners, and light reflecting tapes constituting detectee members 11 are stuck to the two lateral surfaces of the square column-like tray upper portion 220. A linear recession 14 is further provided in the bottom of the cylindrical tray lower portion 210 at the middle portion between the tray-side light passages 12 and 13. This tray is black-colored on the whole and stands opaque.

According to this tray 1, the tray has a two-directional symmetry on the whole. Hence, when trays with vegetables or fruits placed thereon are delivered in the transport path, they can be delivered without so much taking care of the directions of trays with respect to their delivery direction (i.e., have a higher degree of delivery freedom). Also, the tray has a structure wherein the substantially square column-like tray upper portion 220 does not protrude outward from the circumferential edge of the cylindrical tray lower portion 210, and hence, when delivered in the transport path at its part other than the measuring section, the portion at which each tray 1 comes in contact with one another or comes in contact with the wall surfaces of the transport path is the periphery of the cylindrical tray lower portion 210 of the tray. Thus, its contact area can be minimized and the tray is neither caught on the wall surfaces of the transport path nor clogs the transport path. Hence, the tray can be delivered in a greatly improved performance compared with the tray shown in FIG. 1 or FIG. 10.

Figure 13:
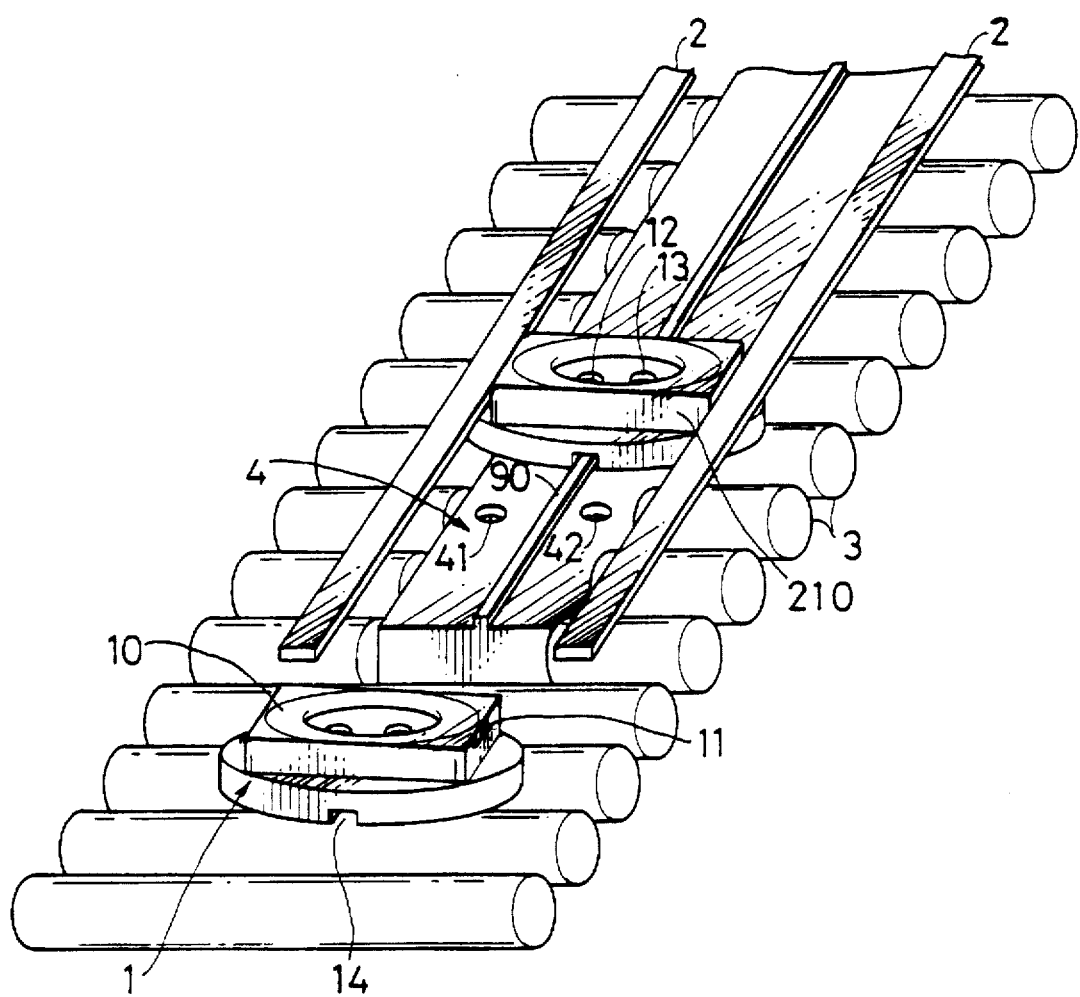
FIG. 13 is a perspective illustration of the main part of a non-destructive taste characteristics measuring apparatus in which the tray of Example 6 is used.

Since the square column-like tray upper portion 220 is worked to have four rounded corners, the trays are smoothly engageable with the guides 2 provided at the measuring section 4 when as shown in FIG. 13 the tray 1 is delivered to the area of the measuring section 4 in the course of the transport path. In addition, the square column-like tray upper portion 210 has four flat surfaces serving as reference surfaces, and hence, when delivered through the measuring section 4, any of the four flat surfaces of the tray upper portion may be allowed to engage with the guides 2. Thus, the tray has the advantage that accurate positional control can be made at the measuring section 4.

Example 7

Figure 14:
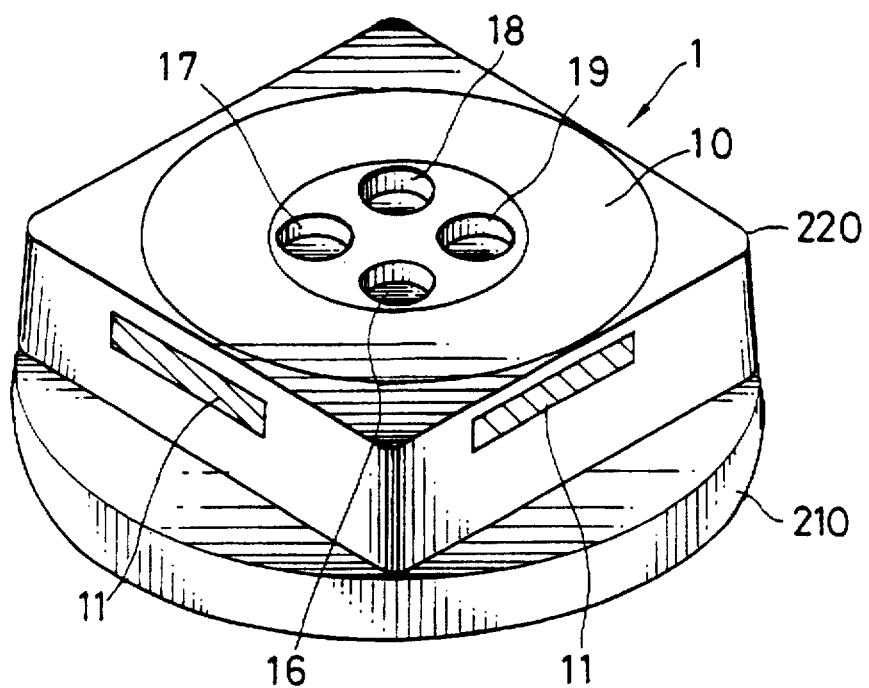
FIG. 14 is a top-side perspective illustration of a tray according to Example 7.

According to the present Example, the tray is substantially the same as the tray according to Example 6 except that, as shown in FIG. 14, four tray-side light passages 16, 17, 18 and 19 are provided in the holding part 10 at its position having a four-directional symmetry, light reflecting tapes constituting detectee members 11 are stuck to the four lateral surfaces thereof, and the linear recession is not formed in the bottom of the cylindrical tray lower portion 210.

This tray has substantially the same function as the tray of Example 6, and also, because of its four-directional symmetry, has the advantage that the degree of delivery freedom is more improved.

Example 8

Figure 15:
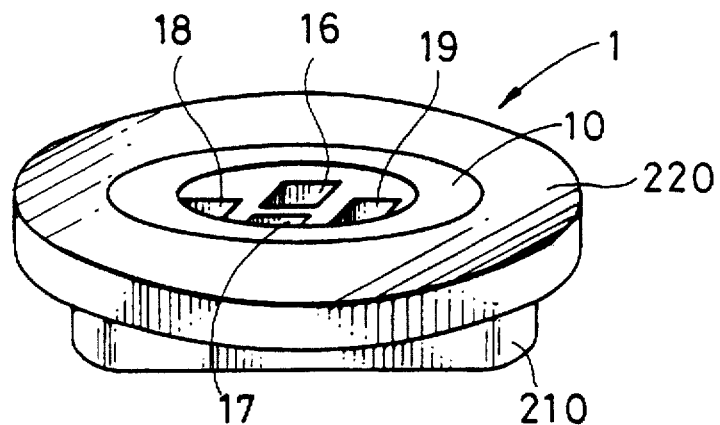
FIG. 15 is a top-side perspective illustration of a tray according to Example 8.
Figure 16:
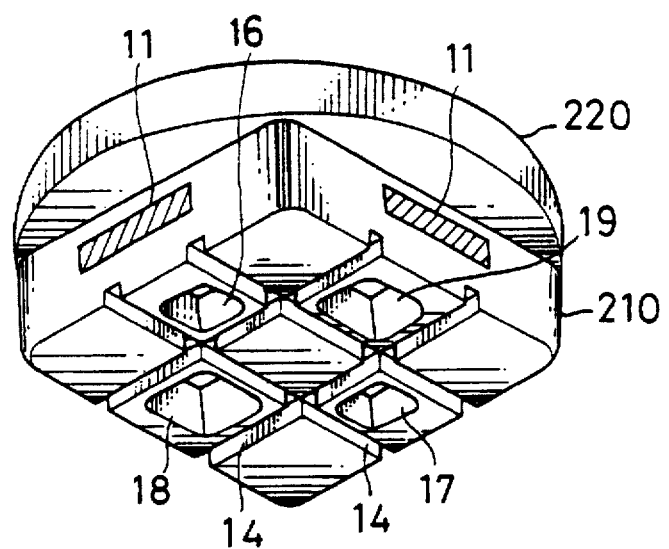
FIG. 16 is a bottom-side perspective illustration of the tray according to Example 8.

According to the present Example, as shown in FIGS. 15 and 16, the tray denoted by reference numeral 1 is constituted chiefly of a cylindrical tray upper portion 220 and a substantially square column-like tray lower portion 210 projecting downward from the cylindrical tray upper portion 220 and not protruding outward from the circumferential edge of the cylindrical tray upper portion 220. Also, the tray upper portion 220 is provided in such a manner that its center overlap with the center of the tray lower portion 210 so that the tray has a four-directional symmetry.

The tray upper portion 220 is provided at the top thereof with the holding part 10 in a conical concave shape, and is provided in the holding part 10 with four tray-side light passages 16, 17, 18 and 19 at its position having the four-directional symmetry. Also, the square column-like tray lower portion 220 is worked to have four rounded corners, and light reflecting tapes constituting detectee members 11 are stuck to the four lateral surfaces of the square column-like tray lower portion 210.

Figure 17:
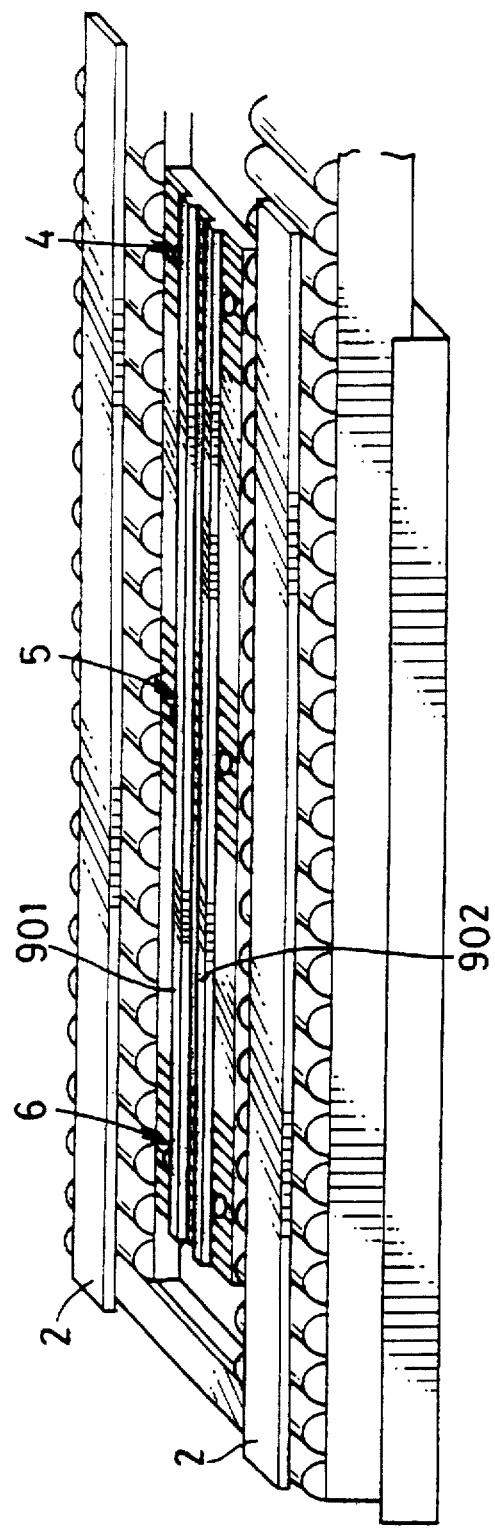
FIG. 17 is a perspective illustration of the main part of a non-destructive taste characteristics measuring apparatus in which the tray of Example 8 is used.

As shown in FIG. 16, grooves 14 in the form of parallel crosses are further provided in the tray lower portion 210 on the back side thereof. The grooves 14 can be slidably loosely fitted to a pair of linear projections 901 and 902 provided as shown in FIG. 17 over measuring sections 4, 5 and 6 of the non-destructive taste characteristics measuring apparatus. Thus, these function as a leakage light preventing means. This tray is also black-colored on the whole and stands opaque.

Figure 18A:
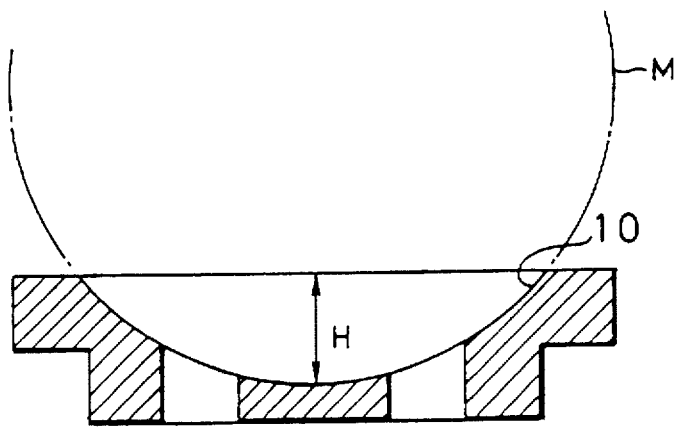
FIG. 18A is a cross-sectional illustration of a tray according to Example 8, and FIG. 18B a cross-sectional illustration of a tray according to Example 7.
Figure 18B:
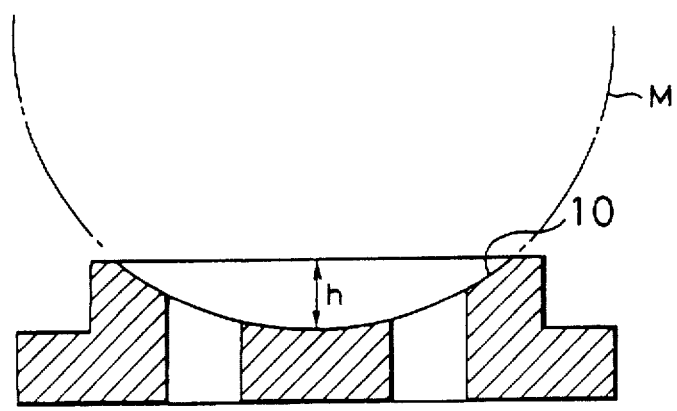

According to this tray 1, the tray has the same advantages as the tray of Example 7. Besides, since the top and bottom are inversed with respect to the tray of Example 7, as shown in FIGS. 18A and 18B the depth H of the holding part 10 can be set larger than the depth h of the holding part 10 of the tray (FIG. 18B) of Example 7, so that the whole tray including the fruit M to be placed thereon can be made lower. Thus, the tray according to the present Example has the advantage that it can be more stably delivered than the tray of Example 7.

Figure 19:
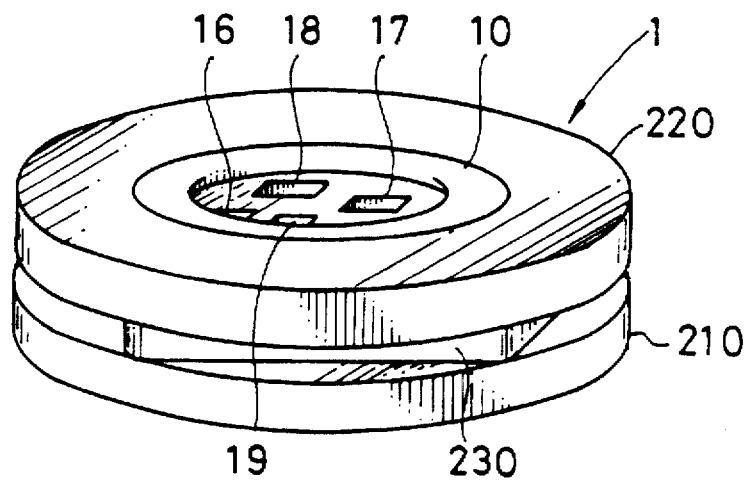
FIG. 19 is a top-side perspective illustration of a modification of Example 8.

FIG. 19 illustrates a modification of the above tray. More specifically, the tray denoted by reference numeral 1 is constituted chiefly of cylindrical tray upper portion 220 and lower portion 210 which have substantially equal diameters and a square column-like tray middle portion provided between these cylindrical tray upper and lower portions 220 and 210 and not protruding outward from the circumferential edges of the cylindrical tray upper and lower portions 220 and 210. Also, the tray upper portion 220, tray middle portion 230 and tray lower portion are provided in such a manner that their centers overlap each other so that the tray has a four-directional symmetry.

The tray upper portion 220 is provided at the top thereof with the holding part 10 in a conical concave shape, and is provided in the holding part 10 with four tray-side light passages 16, 17, 18 and 19 at its position having the four-directional symmetry. Also, the square column-like tray middle portion 230 is worked to have four rounded corners, and light reflecting tapes constituting detectee members (not shown) are stuck to its four lateral surfaces.

The above tray 1 has the functions possessed by the tray 1 shown in FIG. 15, and also, because of a larger bottom area of the tray lower portion 210 than that of the tray of FIG. 15, has the advantage that the former can be more stably delivered than the latter.

Example 9

Figure 20:
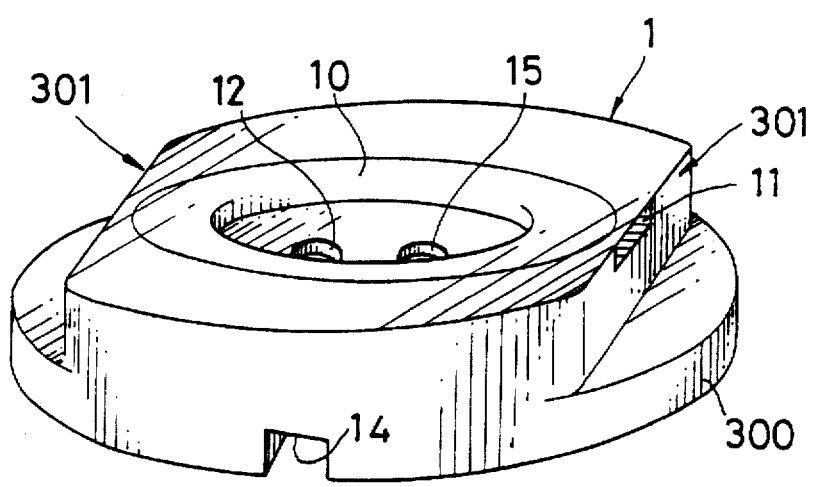
FIG. 20 is a top-side perspective illustration of a tray according to Example 9.

According to the present Example, as shown in FIGS. 20 and 21A, the tray denoted by reference numeral 1, which is made of black ABS (acrylonitrile-butadiene-styrene) resin, is constituted chiefly of a cylindrical tray main body 300 and a pair of planar portions (which constitute reference surfaces) formed by cutting two upper portions of the periphery of the tray main body 300 in parallel to each other.

The tray main body 300 is provided at the top thereof with the holding part 10 in a conical concave shape, and is provided in the holding part 10 with two tray-side light passages 12 and 13 at its position having a two-directional symmetry; the passages having substantially circular cross sections. Also, detectee members 11 comprised of light reflecting tapes are stuck to the upper portions of the pair of planar portions. A linear recession 14 is also provided in the bottom of the tray main body 300 at substantially the middle portion on its bottom side, like that in the tray of Example 6. This tray is black-colored on the whole and stands opaque.

The tray-side light passages 12 and 13 are also respectively constituted chiefly of two openings 12' and 13', substantially cylindrical tubular members 12" and 13" fitted to the insides of the openings 12' and 13' and whose upper ends have been cut in the oblique direction, and semicylindrical fillers 24 and 25 fitted to the inner walls of the tubular members 12" and 13". The fillers 24 and 25 are, as shown in FIG. 21A, each provided on the side the tray-side light passages 12 and 13 face each other so that the shapes of the opening edges of the tray-side light passages 12 and 13 on the side where they face each other may be set to be shapes with straight lines which are parallel to each other and also parallel to the tray delivery direction (shown by an upward arrow in FIG. 21A).

In the non-destructive taste characteristics measuring apparatus in which this tray 1 is used, the emission of light from the end face of the optical fiber is so controlled that it is started immediately before the the opening ends of the tray-side light passages have come into positional agreement with the opening ends of the measurement-side light passages by means of a light incidence timing control means and is continued until such positional agreement is taken away.

Figure 21B:
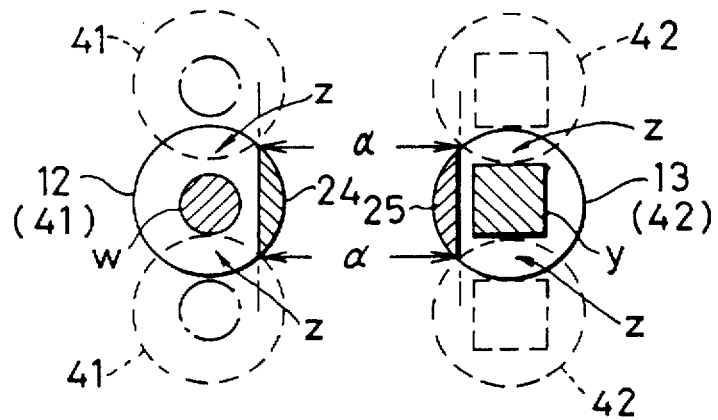
FIG. 21B illustrates how fillers provided in the tray-side light passages of the tray act.

Then, in the tray 1 of the present Example, the semicylindrical fillers 24 and 25 are each provided on the side the tray-side light passages 12 and 13 face each other so that the shapes of the opening edges of the tray-side light passages 12 and 13 on the side where they face each other are set to be shapes with straight lines which are parallel to each other and also parallel to the tray delivery direction. Hence, when the tray with the vegetable or fruit placed thereon is delivered to each measuring section, in the course immediately before the opening ends of the tray-side light passages and the opening ends of the measurement-side light passages come into the positional agreement and until such positional agreement is taken away, the inside edges of the overlapping open areas z formed when the respective opening ends of the tray-side light passages 12 and 13 and measurement-side light passages 41 and 42 overlap each other substantially come into agreement with the inside edges of opening ends of the tray-side light passages 12 and 13 as shown in FIG. 21B by upper-side broken lines, middle-part solid lines and lower-side broken lines. Accordingly, in respect of the overlapping open areas z, the distance α between edges on the side where they face each other becomes substantially constant without regard to the progress of movement of the tray.

Thus, compared with the instance where the tray having no fillers 24 and 25 fitted thereto is used (see FIGS. 38A and 38B), the light path of the laser light emitted from the end face of the optical fiber and reaching the detector can be kept substantially constant in the course immediately before the opening ends of the tray-side light passages 12 and 13 and the opening ends of the measurement-side light passages 24 and 25 come into the positional agreement and until such positional agreement is taken away. Hence, it becomes possible to prevent the phenomenon that the amount of light emergent from the vegetable or fruit and entering the detector y varies in accordance with the progress of movement of the tray. Thus, the present tray has the advantage that the measurement errors caused by the variations of the light path in the measurement of taste characteristics can be held down to a minimum.

Example 10

Figure 22A:
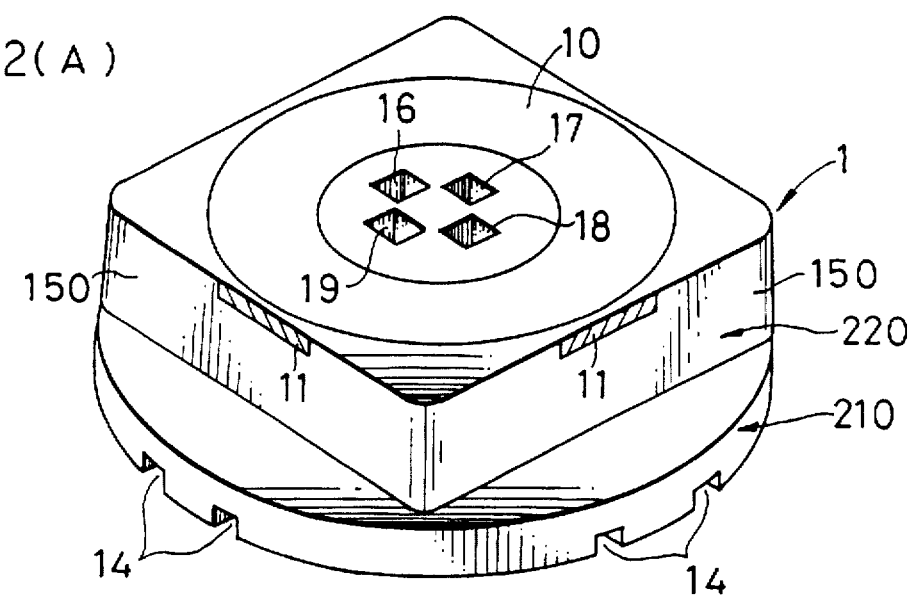
FIG. 22A is a top-side perspective illustration of a tray according to Example 10, and FIG. 22B, a plan view thereof.
Figure 22B:
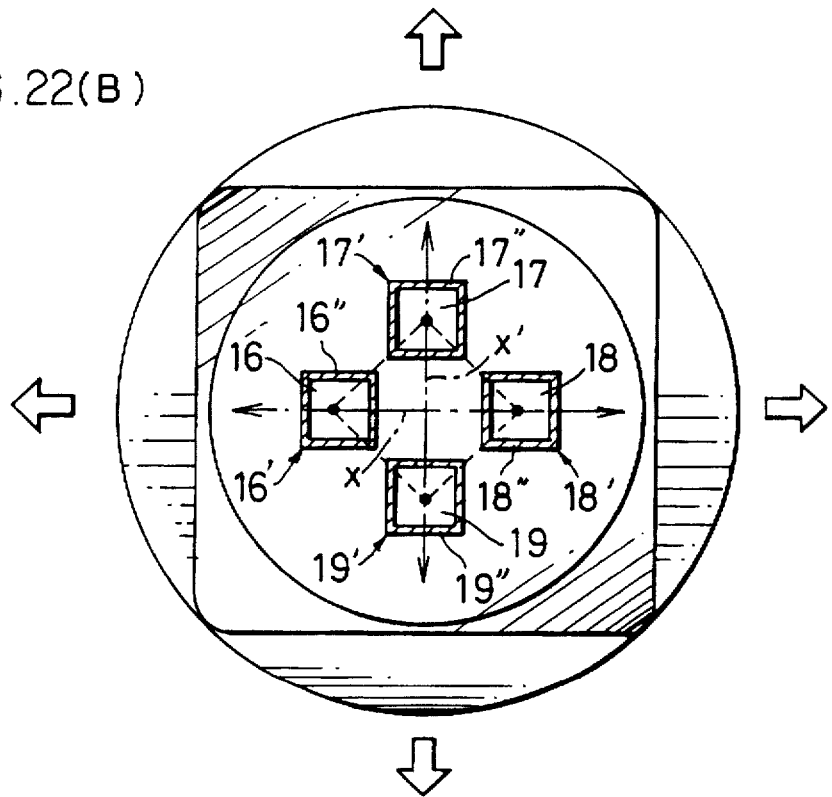

According to the present Example, as shown in FIGS. 22A and 22B, the tray denoted by reference numeral 1 is constituted chiefly of a cylindrical tray lower portion 210 and a substantially square column-like tray upper portion 220 projecting downward from the cylindrical tray lower portion 210 and not protruding outward from the circumferential edge of the cylindrical tray lower portion 210. Also, the tray upper portion 220 is provided in such a manner that its center overlap with the center of the cylindrical tray lower portion 210 so that the tray has a four-directional symmetry.

The tray upper portion 220 is provided at the top thereof with the holding part 10 in a conical concave shape, and is provided in the holding part 10 with four tray-side light passages 16, 17, 18 and 19 at its position having the four-directional symmetry. Also, the square column-like tray upper portion 220 is worked to have four rounded corners, and detectee members 11 comprised of light reflecting tapes are stuck to the four lateral surfaces serving as reference surfaces 150 of the square column-like tray upper portion 220. Grooves 14 in the form of parallel crosses are further provided in the tray lower portion 210 on the back side thereof, like the tray of Example 8.

The tray-side light passages 16, 17, 18 and 19 are also respectively constituted chiefly of four openings 16', 17', 18' and 19', substantially square tubular members 16", 17", 18" and 19" fitted to the insides of the openings 16', 17', 18' and 19' and whose upper ends have been cut in the oblique direction. As shown in FIG. 22B, a quadrangle formed by connecting the centers of opening ends of the respective tray-side light passages 16, 17, 18 and 19 on the side where the vegetable or fruit is placed is in the form of a regular square, and the tray delivery direction is set in the directions of a pair of diagonals x and x' of this regular square. Also, the shapes of the opening edges diagonally x to x' confronting each other, of two sets of tray-side light passages 16, 18 and 17, 18 and on the side where they face each other are set to be shapes with straight lines which are parallel to each other and perpendicular to the direction of the diagonals x and x'. This tray is also black-colored on the whole and stands opaque.

In the tray 1 of the present Example, the quadrangle formed by connecting the centers of opening ends of the respective tray-side light passages 16, 17, 18 and 19 on the side where the vegetable or fruit is placed is in the form of a regular square, and the tray delivery direction is set in the directions of a pair of diagonals x and x' of this regular square. Also, the shapes of the opening edges diagonally x to x' confronting each other, of two sets of tray-side light passages 16, 18 and 17, 18 and on the side where they face each other are set to be shapes with straight lines which are parallel to each other and perpendicular to the direction of the diagonals x and x'. Hence, like the tray of Example 9, the light path of the laser light emitted from the end face of the optical fiber and reaching the detector can be kept substantially constant in the course immediately before the opening ends of the tray-side light passages and the opening ends of the measurement-side light passages come into the positional agreement and until such positional agreement is taken away. Thus, it becomes possible to prevent the phenomenon that the amount of light emergent from the vegetable or fruit and entering the detector varies in accordance with the progress of movement of the tray. The present tray has such an advantage.

Example 11

Figure 23:
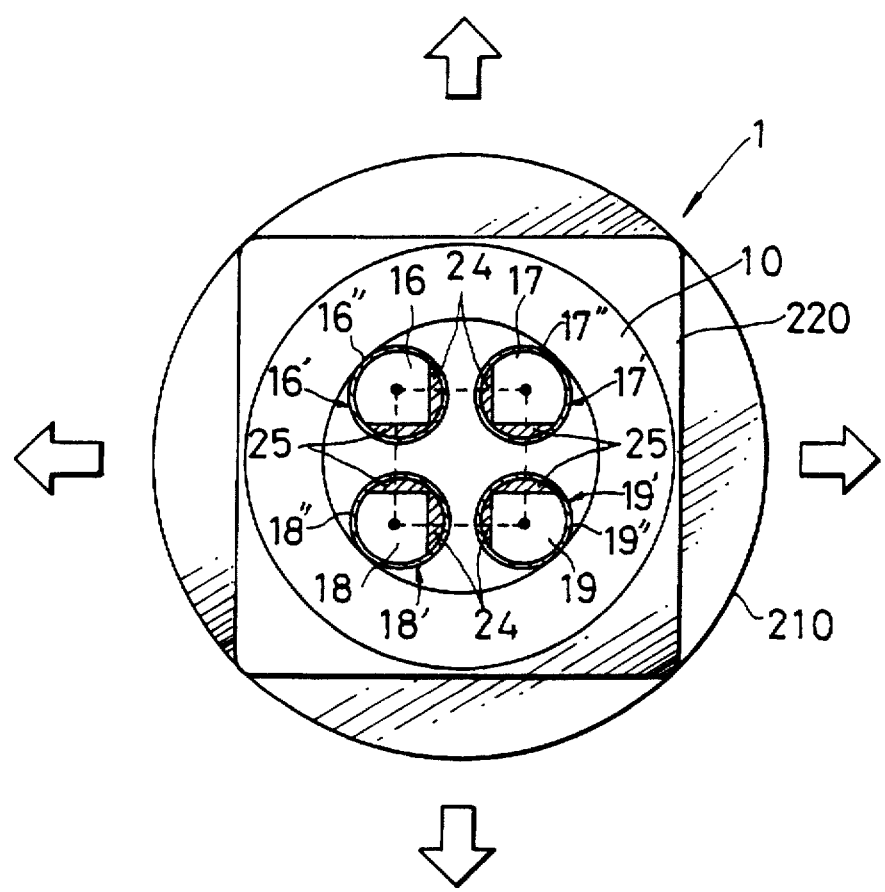
FIG. 23 is a plan view of a tray according to Example 11.

According to the present Example, as shown in FIG. 23, the tray 1 is substantially the same as the tray of Example 10 except that the four tray-side light passages 16, 17, 18 and 19 provided in the holding part 10 of the substantially square column-like tray upper portion 220 have circular transverse cross sections.

More specifically, the tray-side light passages 16, 17, 18 and 19 are respectively constituted chiefly of four openings 16', 17', 18' and 19', tubular members 16", 17", 18" and 19" which are circular in their transverse cross sections, fitted to the insides of the openings 16', 17', 18' and 19' and whose upper ends have been cut in the oblique direction. As shown in FIG. 23, a quadrangle formed by connecting the centers of opening ends of the respective tray-side light passages 16, 17, 18 and 19 on the side where the vegetable or fruit is placed is in the form of a regular square, and the tray delivery direction is set in the directions of each side of this regular square. Also, semicylindrical fillers 24 and 25 are fitted to the inner walls of the tubular members 16", 17", 18" and 19", and, by the action of these fillers 24 and 25, the shapes of the opening edges of the tray-side light passages on the side where they are adjacent to each other are set to be shapes with straight lines which are parallel to each other and also parallel to each side of the quadrangle formed by connecting the centers of opening ends of the respective tray-side light passages. This tray is also black-colored on the whole and stands opaque.

In the tray 1 of the present Example, too, like the tray of Example 10, the light path of the laser light emitted from the end face of the optical fiber and reaching the detector can be kept substantially constant in the course immediately before the opening ends of the tray-side light passages and the opening ends of the measurement-side light passages come into the positional agreement and until such positional agreement is taken away. Thus, it becomes possible to prevent the phenomenon that the amount of light emergent from the vegetable or fruit and entering the detector varies in accordance with the progress of movement of the tray. The present tray also has such an advantage.

Example 12

Figure 25:
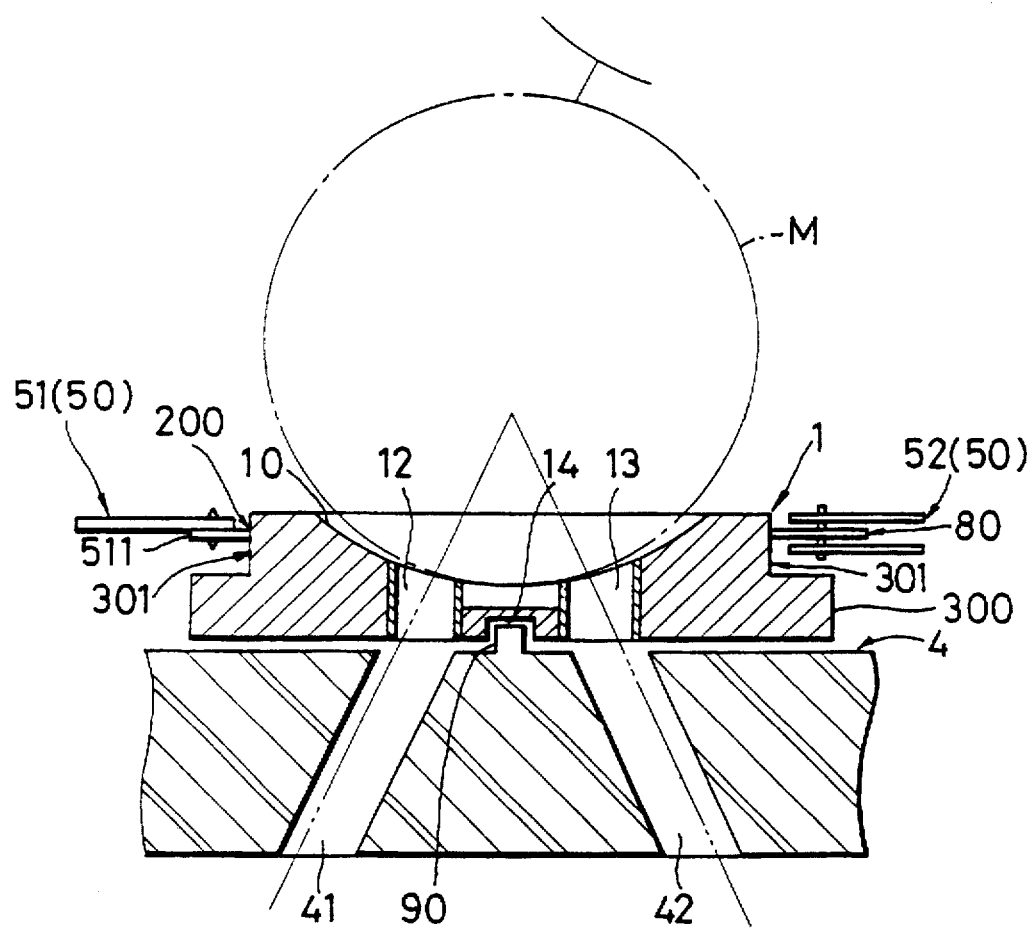
FIG. 25 is a perspective illustration of the tray and measuring section in the non-destructive taste characteristics measuring apparatus according to Example 12.

As shown in FIGS. 24 and 25, a non-destructive taste characteristics measuring apparatus according to the present Example is constituted chiefly of a plurality of trays 1 each having a holding part 10 on which measurement objects vegetables and fruits (muskmelons) M are individually placed; a roller conveyor 3 serving as a tray delivery means that moves the trays 1 at a speed of, e.g., 40 cm/second; three box-like measuring sections 4, 5 and 6 provided in the transport path at appropriate intervals; a delivery position control means 50 provided in the length direction of the transport path to control the delivery position of the trays 1; a vegetable or fruit presence-absence sensor (not shown) provided in the vicinity of each of the measuring section 4, 5 and 6 to judge the presence or absence of the vegetables and fruits M on the trays 1; a position sensor (not shown) similarly provided in the vicinity of each of the measuring section 4, 5 and 6 to detect a detectee member 11 provided to each tray 1, to find out the points of time at which the trays 1 and the measuring sections 4, 5 and 6 come into positional agreement; semiconductor lasers (not shown) that emit light to the muskmelons M at the respective measuring sections 4, 5 and 6; and detectors (not shown) which light rays emergent from the muskmelons M enter at the respective measuring sections 4, 5 and 6. A linear projection 90 is also provided at the middle portion on the top side of the measuring sections 4, 5 and 6.

As shown in FIG. 25, the above tray 1, which is made of black ABS (acrylonitrile-butadiene-styrene) resin, is constituted chiefly of a cylindrical tray main body 300 and a pair of planar portions (which constitute reference surfaces) formed by cutting two upper portions of the periphery of the tray main body 300 in parallel to each other.

The tray main body 300 is provided at the top thereof with the holding part 10 in a conical concave shape, and is provided in the holding part 10 with two tray-side light passages 12 and 13 at its position having a two-directional symmetry; the passages having substantially circular cross sections. Also, detectee members (not shown) comprised of light reflecting tapes are stuck to the upper portions of the pair of planar portions 301. A linear recession 14 is also provided in the bottom of the tray main body 300 at substantially the middle portion on its bottom side, which functions like that in the tray of Example 9. This tray is black-colored on the whole and stands opaque.

Figure 26:
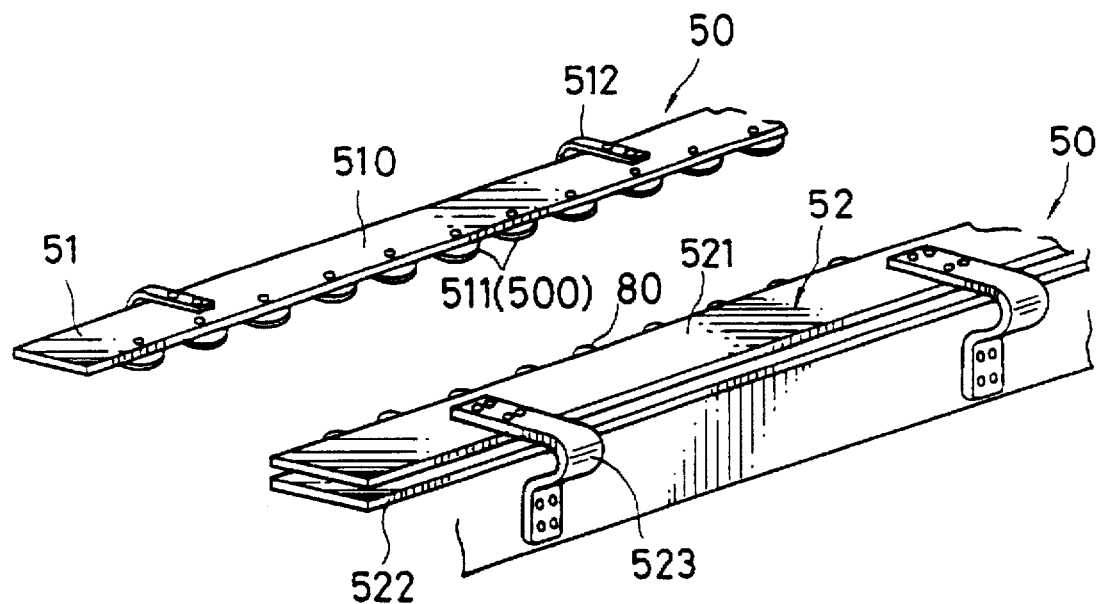
FIG. 26 is a perspective illustration of a tray delivery position control means used in the non-destructive taste characteristics measuring apparatus according to Example 12.
Figure 27:
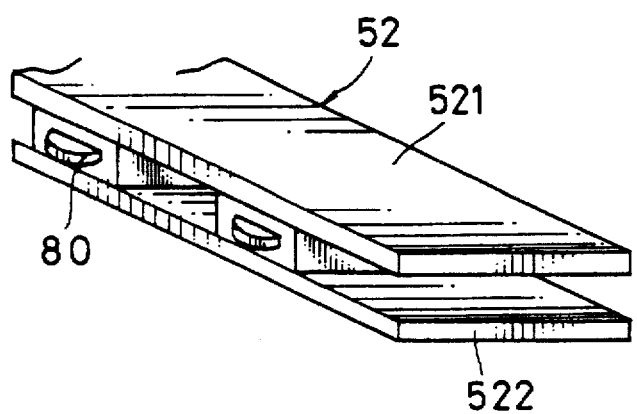
FIG. 27 is a partial perspective illustration of a second side bar that constitutes part of the tray delivery position control means shown in FIG. 26.

The delivery position control means 50 is, as shown in FIGS. 24, 26 and 27, constituted chiefly of a first side bar 51 provided in the length direction of the transport path, and a second side bar 52 provided on the side opposite to the first side bar 51 and having a pressing means 80 that presses against the first side bar 51 the tray 1 delivered through the transport path.

The first side bar 51 is, as shown in FIG. 26, constituted of a first side bar main body 510, a plurality of rollers (rotary disks) 511 provided to this first side bar main body 510, and a fixing member 512 that fixes the first side bar main body 510 to the one side edge of the transport path. Since the rollers 511 engage with one of the planar portions (constituting reference surfaces) 301 of the tray 1, the surfaces of rollers that come in contact with the tray 1 form guide faces 500.

Figure 28:
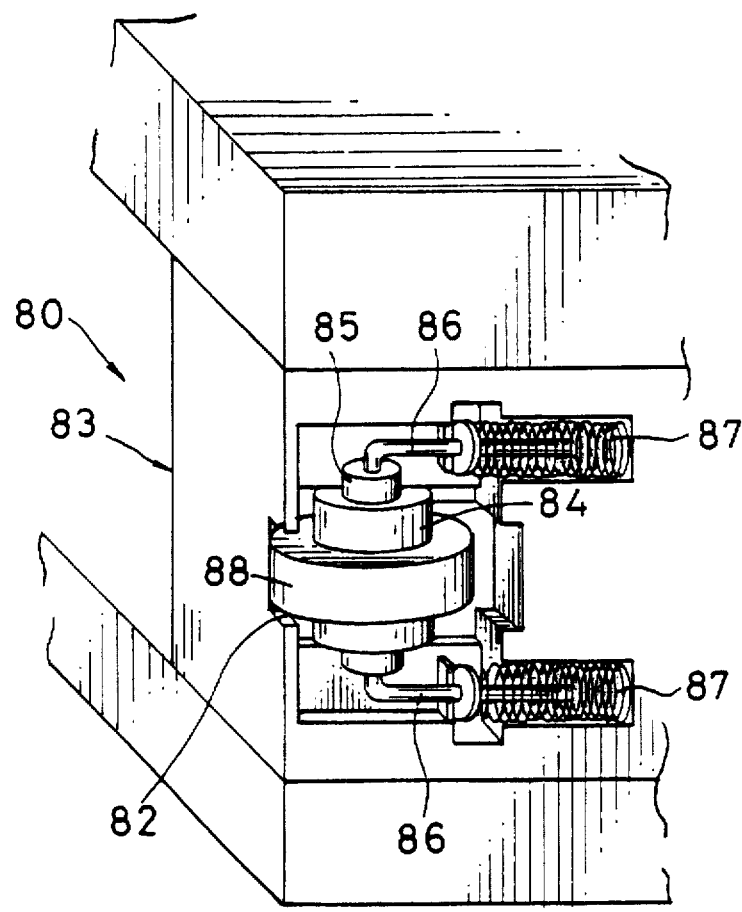
FIG. 28 is a partially broken perspective illustration of a pressing means incorporated in the second side bar shown in FIG. 27.
Figure 29:
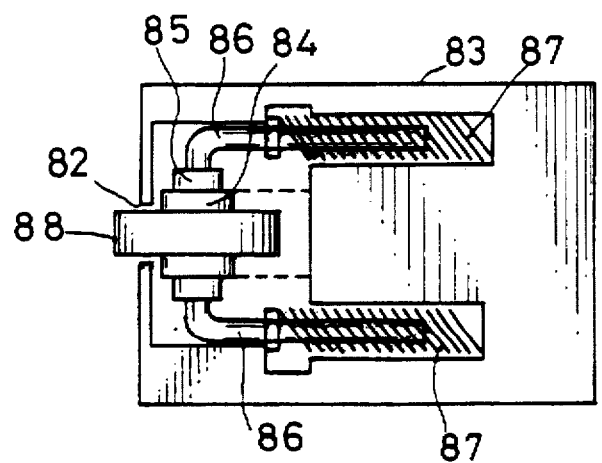
FIG. 29 is a cross-sectional illustration of the pressing means shown in FIG. 28.

Meanwhile, the second side bar 52 is, as shown in FIGS. 26 and 27, constituted chiefly of a pair of plate-like second side bar main bodies 521 and 522 provided face to face at given intervals and formed of a metal such as iron, a pressing means 80 provided in the gap between these second side bar main bodies 521 and 522, and a fixing member 523 that fixes the second side bar main bodies 521 and 522 to the other side edge of the transport path. The pressing means 80 is, as shown in FIGS. 28 and 29, constituted of a pressing member holder 83 having an opening 82 on the transport path side, a roller (rotary disk) 88 provided projectably from the opening 82 within the pressing member holder 83, a pair of support member 86 movably supporting the roller 88 at its shaft 85, and a pair of spring members 87 pressing these supporting members to push out the roller 88 to the transport path side. A guide roller 84 that guides the projecting motion of the roller 88 is also inserted between the roller 88 and the shaft 85.

The pressing means 80 of the second side bar 52 presses the tray 1 delivered between the first side bar 51 and the second side bar 52 to bring one reference surface 301 of the tray into engagement with the guide faces 500 (as describe above, the contact surfaces engageable with the tray 1 in the plurality of rollers 511 provided to the first side bar main body 510 form the guide faces; see FIG. 26) of the first side bar 51, so that the trays 1 with vegetables and fruits placed thereon can be accurately delivered to proper positions of the respective measuring sections 4, 5 and 6 without causing the rocking motion of the trays 1. Also, by the action of the plurality of rollers 511 provided to the first side bar 51 and the action of the rollers 80 each constituting part of the pressing means 80 of the second side bar 52, the frictional force accompanied with the contact between the side bars 51 and 52 and the tray 1 is decreased, and hence no difficulty may occur in the delivery performance of the tray in the transport path.

The present non-destructive taste characteristics measuring apparatus is also additionally provided with a direction control mechanism for arranging the trays 1 in a proper direction when the trays 1 are delivered to the area of the transport path in which the three measuring sections 4, 5 and 6 are successively provided. More specifically, as shown in FIG. 30, this direction control mechanism, 700, is provided in a guide path formed directly before the part where the measuring sections are successively provided, and is constituted of a linear projection guide portion 72 provided at substantially the middle of the guide path and continuous to the linear projection 90 formed throughout the measuring sections, and a pair of delivery belts 73 and 74 provided on both edge sides of the guide path and having delivery speeds different from each other. In order to make the tray 1 readily run up the linear projection guide portion 72, as shown in FIG. 30 the height of the linear projection guide portion 72 on the entrance side is set lower than the linear projection 90. Also, its height is so set as to become gradually greater toward the forward portion of the guide path and finally become equal to the height of the linear projection 90. Since in the guide path the tray 1 is delivered by the aid of the delivery belts 73 and 74, the rollers within the area of the guide portion require no driving power, and hence they are comprised of freely rotatable rollers. The delivery belts 73 and 74 are so set as to be driven at a speed of 45 cm/second for one of them and 35 cm/second for the other.

Since in this direction control mechanism 700 the pair of delivery belts 73 and 74 having delivery speeds different from each other are provided on both edge sides of the guide path, the tray 1 delivered to the area of the guide path is sent forward while being rotated as shown by an arrow in FIG. 30, on account of the difference in delivery speed. It is stopped being rotated after the linear projection guide portion 72 in the guide path has been fitted to the linear recession 14 of the tray, and thereafter, in the state that the tray is put into a proper direction, it is delivered to the area of the transport path in which the measuring sections are successively provided.

In this way, in the non-destructive taste characteristics measuring apparatus, the power sources 100 are switched on at every time when the tray 1 with the fruit M placed thereon passes through the respective measuring sections 4, 5 and 6. In the measuring section 4, laser light of 930 nm is emitted for 20 milliseconds. As shown in FIG. 25, this laser light is made incident on the fruit M though the measurement-side light passage 41 and the tray-side light passage 12 and then the light emergent from the fruit M enters the detector (not shown) through the tray-side light passage 13 and the measurement-side light passage 42. Similarly, subsequently in the measuring section 5, laser light of 910 nm is emitted for 20 milliseconds, and, in the measuring section 6, laser light of 880 nm is emitted for 20 milliseconds. Each light emergent from the fruit M enters each detector (not shown), and the taste characteristics such as sugar content of the fruit M is measured. The apparatus is so designed that these are measured in a dark room.

According to this non-destructive taste characteristics measuring apparatus, the delivery position control means 50 that controls the delivery position of the trays 1 is provided in the length direction of the transport path, and hence the trays 1 with vegetables and fruits placed thereon as shown in FIG. 25 can be accurately delivered to proper positions of the respective measuring sections 4, 5 and 6 without causing the rocking motion of the trays 1.

Accordingly, the light path of the emitted laser light reaching the detector may less change in length and also light rays having different wavelengths can be successively made incident on the fruit M at substantially the same position thereof, so that the differences in reflectance of the respective light rays can be minimized. Also, the information of light can be obtained at substantially the same position inside the fruit M, and hence the measurement errors can be greatly decreased.

In this non-destructive taste characteristics measuring apparatus, as the structural means for decreasing the frictional force accompanied with the contact between the side bars and the trays, the constitution in which the first side bar 51 provided with the rollers 511 as shown in FIG. 26 may be replaced with a constitution wherein the first side bar is made up using a plate-like bar having no rollers 511 and a tray is used which has such a structure that its reference surface 301 engaging with the first side bar is provided with a roller having the same functions as the rollers 511. If, however, the tray is provided with such a roller on each side of the reference surfaces 301 of the tray shown in FIG. 25, the roller on one side may overlap with the roller 88 of the second side bar 52 to provide a possibility of causing a difficulty in its delivery performance. Hence, such a roller must be provided only on one reference surface 301, and also, since thereby the reference surface is limited to one site, the delivery direction of the tray in each measuring section can be controlled to one direction (i.e., the tray has no two-directional symmetry for its delivery direction).

In the present Example, the above delivery position control means 50 provided in the respective measuring sections 4, 5 and 6 has the structure wherein as shown in FIG. 24 it is constituted chiefly of a pair of first side bar 51 and second side bar 52 continuously provided in the length direction of the transport path. This may be replaced with a structure wherein a plurality of delivery position control means are intermittently provided for each of the measuring sections 4, 5 and 6. In the latter case, it is necessary to make adjustment so that the guide faces of the respective delivery position control means at the measuring sections 4, 5 and 6 are set along the same line (i.e., to make adjustment so that the areas where the reference surface of a tray engage with the guide faces of the respective delivery position control means are set along substantially the same line identical in the respective measuring sections 4, 5 and 6).

Example 13

Figure 31:
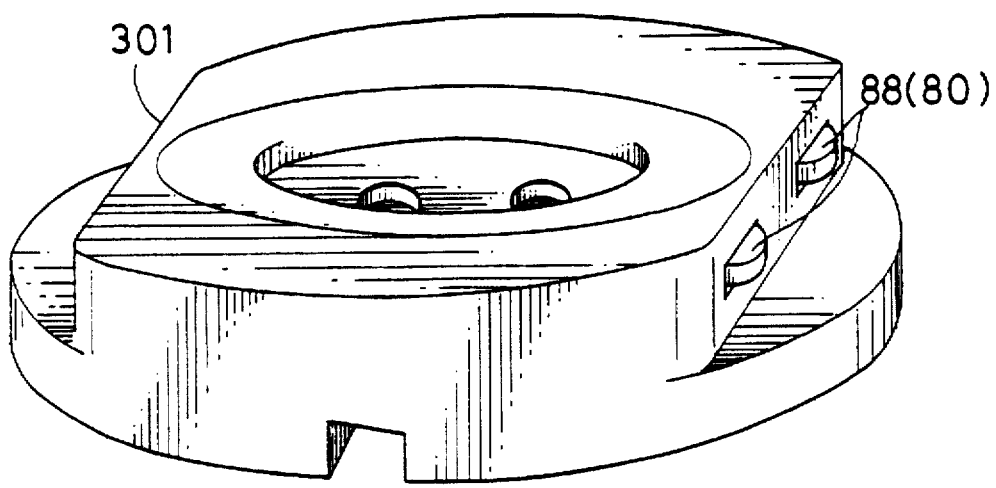
FIG. 31 is a top-side perspective illustration of a tray according to Example 13.
Figure 32:
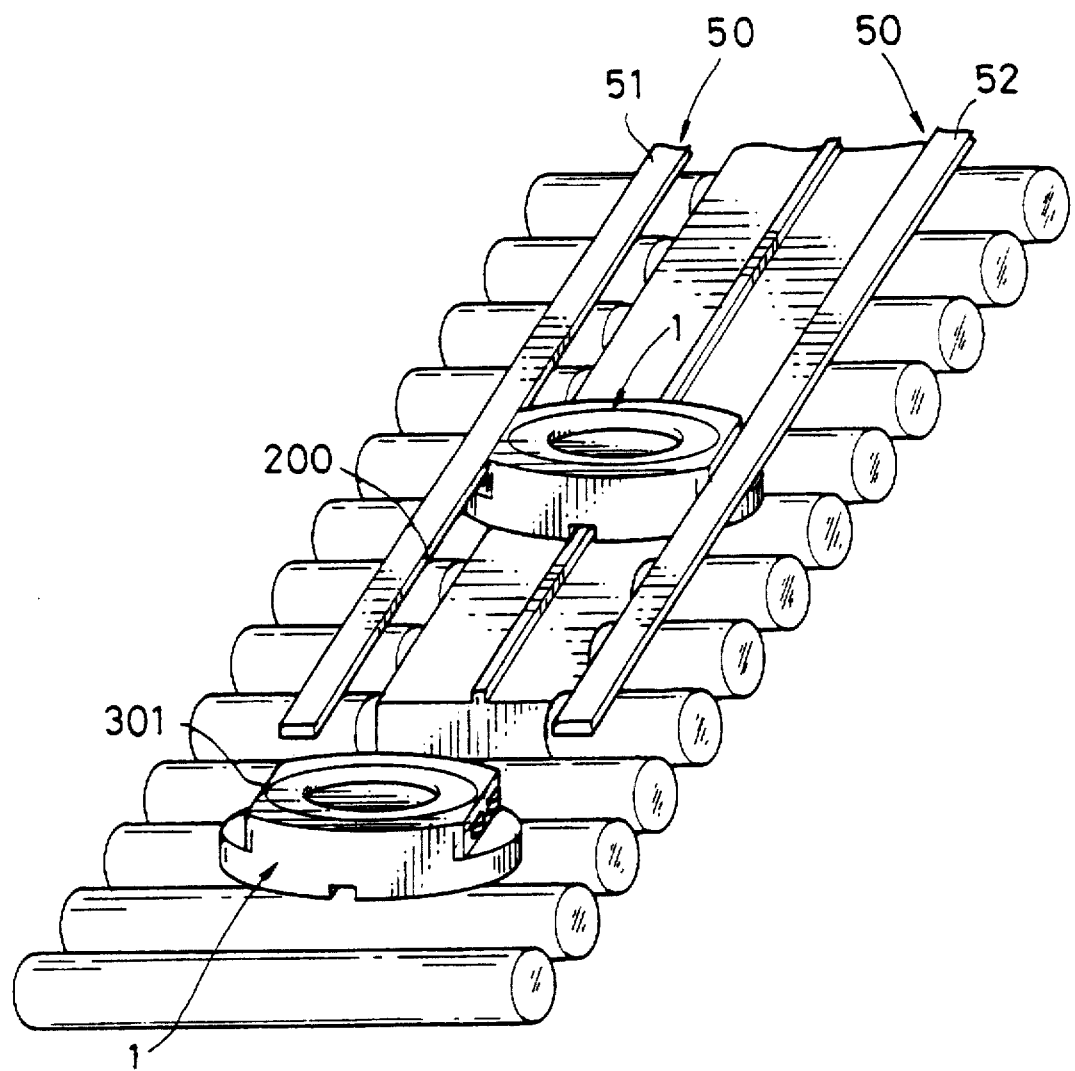
FIG. 32 is a perspective illustration of the main part of a non-destructive taste characteristics measuring apparatus in which the tray of Example 13 is used.

In the present Example, the non-destructive taste characteristics measuring apparatus is substantially the same as the non-destructive taste characteristics measuring apparatus according to Example 12 except that a tray 1 as shown in FIG. 31 is used in which rollers 88 having substantially the same structure as that shown in FIG. 28 is provided to one reference surface 301 of the tray shown in FIG. 25 to use it as the pressing means, and rollers having substantially the same function as the rollers 511 are provided to the other reference surface 301 so that their contact faces engaging with the guide faces of the delivery position control means are made to function as a reference surface of the delivery position control means, and that the constitution of the delivery position control means 50 is changed as shown in FIG. 32 with some modification of the tray 1.

More specifically, this tray 1 is made up using the same material as the tray of Example 12, and, as shown in FIG. 31, rollers 88 having substantially the same structure as those shown in FIG. 28 are provided on one side of the pair of reference surfaces as formed in Example 12, to constitute a pressing means 80. Meanwhile, rollers having the same function as the rollers 511 are provided to the other reference surface 301 so that their contact faces engaging with the guide faces of the delivery position control means are made to function as a reference surface of the delivery position control means. In this tray 1, the reference surface is limited to one site, but the tray has the two-directional symmetry for its delivery direction. The reason why it has will be described later. This tray is also black-colored on the whole and stands opaque.

As for the delivery position control means 50, it is formed of the same material as used in Example 12, and is constituted of a first side bar 51 having a guide face 200 and a second side bar 52 provided opposingly thereto (see FIG. 32).

In this non-destructive taste characteristics measuring apparatus, in the course where the tray 1 as shown in FIG. 31 is delivered between the first side bar 51 and the second side bar 52, the rollers 88 serving as the pressing means 80 of the tray 1 press the second side bar 52, and, by the aid of its counterforce, the peripheries of the rollers made to function as the reference surface 301 of the tray 1 is brought into engagement with the guide face (the end face engaging with the reference surface 301 of the tray in the first side bar main body constitutes the guide face because, different from the case of Example 12, the first side bar 51 is not provided with the plurality of rollers 511; see FIG. 32). Hence, the trays 1 with vegetables and fruits placed thereon can be accurately delivered to proper positions of the respective measuring sections without causing the rocking motion of the trays 1. Also, the side bars 51 and 52 and the tray 1 engage with one another through the rollers made to function as the reference surface 301 of the tray and the rollers 88 serving as the pressing means 80, and hence, like the non-destructive taste characteristics measuring apparatus according to Example 12, no difficulty may occur in the delivery performance of the tray in the transport path.

When the tray 1 is delivered between the first side bar 51 and the second side bar 52 in the state that its front and rear of the tray are in reverse, the rollers 88 serving as the pressing means 80 of the tray 1 press the first side bar 51 on the contrary as the case described above, and, by the aid of its counterforce, the peripheries of the rollers made to function as the reference surface 301 of the tray 1 is brought into engagement with the guide face of the second side bar 52. Thus, while being guided by the end face of the second side bar 52, the tray 1 can be accurately delivered to proper positions (the delivery position of the tray 1 is a little different from the case when the tray is delivered while its reference surface engages with the guide face 200 of the first side bar 51, but by no means different in that the tray is delivered through the identical areas of the respective measuring sections, and accordingly the tray can be delivered to proper positions of the measuring sections). Accordingly, like the case when the tray is delivered while its reference surface engages with the guide face 200 of the first side bar 51, the light path of the emitted laser light reaching the detector may less change in length and also light rays having different wavelengths can be successively made incident on the vegetable or fruit at substantially the same position thereof, so that the differences in reflectance of the respective light rays can be minimized. When in this way the tray 1 is delivered between the first side bar 51 and the second side bar 52 in the state that its front and rear of the tray are in reverse, the end face at which the second side bar 52 engages with the reference surface of the tray 1 constitutes the guide face 200, and the tray has the two-directional symmetry for its delivery direction even though the reference surface is limited to one site.

In the present Example, the tray having the rollers 88 serving as the pressing means 80 and the rollers having the same function as the rollers 511 is used. This tray 1 may alternatively have a structure wherein the rollers having the same function as the rollers 511 are not provided, or, in the case when the tray of this type is used, may be so constituted that the side bar having the rollers 511 as used in Example 12 (see FIG. 26) is used so as to decrease frictional force. Still alternatively, the tray may be so constituted as to decrease frictional force by the use of a first side bar 51 and a second side bar 52 to each of which a cross-sectionally semicylindrical belt-like molded product made of a slippery plastic material such as polytetrafluoroethylene has been fixed to its end face.

Example 14

Figure 33:
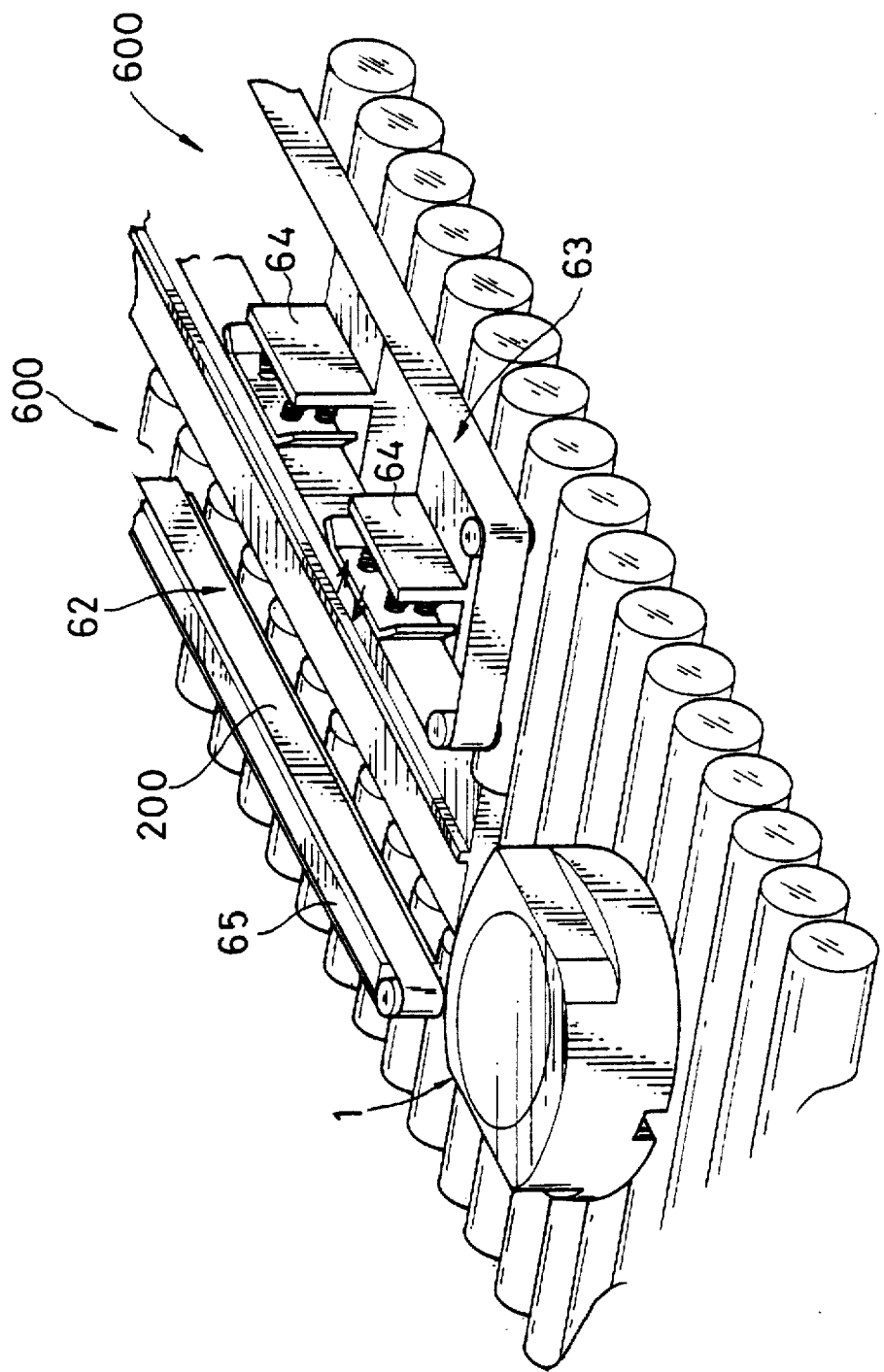
FIG. 33 is a perspective illustration of the constitution of a tray delivery position control means used in a non-destructive taste characteristics measuring apparatus according to Example 14.

In the present Example, the non-destructive taste characteristics measuring apparatus is substantially the same as the non-destructive taste characteristics measuring apparatus according to Example 12 except that the delivery position control means 50 as shown in FIG. 26 is replaced with a delivery position control means 600 as shown in FIG. 33.

More specifically, this delivery position control means 600 is, as shown in FIG. 33, constituted chiefly of a first delivery belt 62 provided with a guide face plate member 65 at the middle thereof, and a second delivery belt 63 opposingly provided at a stated interval with respect to this first delivery belt 62. Also, a pressing means 64 that presses the delivery surface of the second delivery belt 63 against the first delivery belt 62 is provided at the portion corresponding to each measuring section of the second delivery belt 63. In this non-destructive taste characteristics measuring apparatus, since the tray is delivered in the transport path by the aid of the first delivery belt 62 and second delivery belt 63, the rollers in the transport path require no driving power, and hence they are comprised of freely rotatable rollers like the case of the direction control mechanism previously described.

In this non-destructive taste characteristics measuring apparatus, the pressing means 64 presses the tray 1 delivered while being held between the first delivery belt 62 and the second delivery belt 63 to bring one reference surface of the tray into engagement with the guide face 200 (in this case, the contact surfaces where the first delivery belt 62 supported by the guide face plate member 65 comes into contact with the reference surface 301 of the tray forms the guide face; see FIG. 33) of the first delivery belt 62, so that the trays 1 with vegetables and fruits placed thereon can be accurately delivered to proper positions of the respective measuring sections without causing the rocking motion of the trays 1. Also, by the action of the first delivery belt 62 and second delivery belt 63, no difficulty may occur in the delivery performance of the tray 1 in the transport path.

In place of the constitution formed of the second delivery belt 63 and pressing means 64, the delivery position control means may be constituted using, for example, the second side bar 52 (see FIG. 26) used in Example 12, having the rollers 88 serving as the pressing means 80.

What is claimed is:

1. A non-destructive taste characteristics measuring apparatus comprising a plurality of trays on which measurement objects vegetables and fruits are to be placed, a transport means for successively delivering the trays at appropriate intervals, and a measuring section provided in the course of a transport path and at which light is made incident on each vegetable or fruit so as to pass from the outside to the inside thereof and the intensity of light emergent from the vegetable or fruit is measured to determine the taste characteristics of the vegetables and fruits, wherein;

said trays are each provided in a vegetable or fruit holding part of the tray, with at least two tray-side light passages one opening ends of which are so made as to come in contact with the lower periphery of the vegetable or fruit and the other ends of which stand open outward at the bottom of the tray; said passages extending in the thickness direction of the tray at its part where the vegetable or fruit is held; and said measuring section has at least two measurement-side light passages one opening ends of which are positionally adjustable to the opening ends of said tray-side light passages within said transport path at its part facing the bottom of said tray, and is provided with i) a means for making light incident on the vegetable or fruit through one of the measurement-side light passages and one of the tray-side light passages which is positionally adjusted thereto and ii) a detector which the light emergent from the vegetable or fruit enters through the other tray-side light passage and the other measurement-side light passage positionally adjusted thereto, to measure the taste characteristics of the vegetable or fruit.

2. The non-destructive taste characteristics measuring apparatus according to claim 1, wherein said trays are each provided with three tray-side light passages in the vegetable or fruit holding part of the tray, and said measuring section has three measurement-side light passages opening ends of which are positionally adjustable to the opening ends of the respective tray-side light passages; said measuring section being provided with i) a means for making light incident on the vegetable or fruit through one measurement-side light passage and one tray-side light passage positionally adjusted thereto and ii) two detectors which the light emergent from the vegetable or fruit enters through the remaining two tray-side light passages and two measurement-side light passage positionally adjusted thereto.

3. The non-destructive taste characteristics measuring apparatus according to claim 1, wherein said trays are each provided with four tray-side light passages in the vegetable or fruit holding part of the tray, and said measuring section has four measurement-side light passages opening ends of which are positionally adjustable to the opening ends of the respective tray-side light passages; said measuring section being provided with i) a means for simultaneously making light rays with the same wavelengths incident on the vegetable or fruit through two measurement-side light passages and two tray-side light passages positionally adjusted thereto and ii) two detectors which the light rays emergent from the vegetable or fruit respectively enters through the remaining two tray-side light passages and two measurement-side light passages positionally adjusted thereto.

4. The non-destructive taste characteristics measuring apparatus according to claim 1, wherein said trays are each provided with four tray-side light passages in the vegetable or fruit holding part of the tray, and said measuring section has two measurement-side light passages opening ends of which are positionally adjustable to each two sets of the opening ends of the respective tray-side light passages; said measuring section being provided with i) a means for successively making light rays incident on the vegetable or fruit through one measurement-side light passage and two tray-side light passage successively positionally adjusted thereto and ii) a detector which the light emergent from the vegetable or fruit successively enters through the remaining two tray-side light passages and the other measurement-side light passage successively positionally adjusted thereto.

5. The non-destructive taste characteristics measuring apparatus according to any one of claims 1 to 4, wherein a light-transmissive cover member that covers the respective tray-side opening ends of the measurement-side light passages is provided on the measuring section over its surface facing the tray, and the light-transmissive cover member is provided with a cleaning means for removing the foreign matter having adhered to the member.

6. The non-destructive taste characteristics measuring apparatus according to any one of claims 1 to 4, wherein a pad member is provided at each opening end of the tray-side light passages on its side where the vegetable or fruit is placed; said pad member being formed of a porous material and capable of being deformed by the weight of the vegetable or fruit when it is placed on the tray, to close the gaps between the periphery of the vegetable or fruit and the opening ends of the tray-side light passages.

7. The non-destructive taste characteristics measuring apparatus according to claim 6, wherein said pad member is provided on the side of each opening end of the tray-side light passages via a contractible tubular member communicating with each tray-side light passage.

8. The non-destructive taste characteristics measuring apparatus according to any one of claims 1 to 4, wherein a leakage light preventing means is provided on the surfaces facing each other between the tray and the measuring section so that the light incident on the vegetable or fruit through the tray-side light passage and the measurement-side light passage positionally adjusted thereto is prevented from leaking into other measurement-side light passage.

9. The non-destructive taste characteristics measuring apparatus according to claim 8, wherein said leakage light preventing means comprises a linear projection provided on the top of the measuring section along its tray delivery direction and a linear recession provided in the bottom of the tray on the side of the measuring section and slidably loosely fittable to the linear projection.

10. The non-destructive taste characteristics measuring apparatus according to claim 9, wherein the transport means is provided with a tray direction control means at the lead-in portion of the transport path where the measuring section is provided; said tray direction control means comprising a projected guide provided at the middle of the width direction of the transport path in its tray delivery direction and so provided as to be loosely fitted to the linear recession positionally adjustable to the linear projection and formed in the bottom of the tray, and at least a pair of delivery means provided on both side edges of the transport path where the projected guide is provided and capable of coming in contact with the side walls of the tray and being driven at different delivery speeds.

11. The non-destructive taste characteristics measuring apparatus according to any one of claims 1 to 4, wherein the inner peripheral walls of the tray-side light passage and measurement-side light passage are endowed with a high light-reflectivity.

12. The non-destructive taste characteristics measuring apparatus according to claim 1, wherein a plurality of measuring sections are provided in said transport path, and each of the measuring sections is provided with a tray delivery position control means for controlling the delivery position of the tray while bringing the reference surface of the tray into engagement with a guide face provided in the tray delivery direction.

13. The non-destructive taste characteristics measuring apparatus according to claim 12, wherein said tray delivery position control means comprises a pair of side bars provided at an appropriate interval on both side edges of the transport path at each measuring section, and a pressing means fixed to one of the side bars and pressing a tray to be delivered between the side bars, against the other side bar to bring the reference surface of the tray into engagement with a guide face of the latter's side bar.

14. The non-destructive taste characteristics measuring apparatus according to claim 12, wherein said tray delivery position control means comprises a pair of side bars provided at an appropriate interval on both side edges of the transport path at each measuring section, and a pressing means fixed to a tray to be delivered between the side bars and pressing one of the side bars to exert a counterforce to bring the reference surface of the tray into engagement with a guide face of the other side bar.

15. The non-destructive taste characteristics measuring apparatus according to claim 12, wherein said tray delivery position control means comprises a delivery belt provided on one side edge of the transport path at each measuring section so as to have the function as the guide face and be brought into contact with the reference surface of a tray, to deliver the tray, a side bar provided on the other side edge of the transport path and at a portion facing the delivery belt, and a pressing means fixed to the side bar, for bringing the reference surface of the tray to be delivered between the side bar and the delivery belt, into contact with a guide face of the delivery belt.

16. The non-destructive taste characteristics measuring apparatus according to any one of claims 13 to 15, wherein a plurality of rollers are provided at one of contacting surfaces where the side bar and the tray come into contact, so as to decrease the frictional force accompanying the contact.

17. The non-destructive taste characteristics measuring apparatus according to any one of claims 13 to 15, wherein a plurality of rollers are provided at one of contacting surfaces where the side bar and the tray come into contact, so as to decrease the frictional force accompanying the contact; and said pressing means comprises a resilient material layer provided on the periphery of each roller.

18. The non-destructive taste characteristics measuring apparatus according to any one of claims 13 to 15, wherein a plurality of rollers are provided at one of contacting surfaces where the side bar and the tray come into contact, so as to decrease the frictional force accompanying the contact; and said pressing means comprises a supporting means for movably supporting the axis of each roller, and a spring means for pressing the support means to push out the periphery of the roller against the contact surface side of the side bar or tray.

19. The non-destructive taste characteristics measuring apparatus according to claim 12, wherein said tray delivery position control means comprises a first delivery belt provided on one side edge of the transport path at each measuring section so as to have the function as the guide face and be brought into contact with the reference surface of a tray, to deliver the tray, a second delivery belt provided on the other side edge of the transport path and at a portion facing the first delivery belt, and a pressing means provided on the second delivery belt, for bringing the reference surface of the tray to be delivered between the first delivery belt and the second delivery belt, into contact with a guide face of the first delivery belt.

* * * * *